(12) United States Patent
Major et al.

(10) Patent No.: US 9,216,089 B2
(45) Date of Patent: Dec. 22, 2015

(54) METHOD OF SURGICALLY PREPARING A PATIENT'S TIBIA

(71) Applicant: DEPUY (IRELAND), Cork (IE)

(72) Inventors: Lisa M. Major, Warsaw, IN (US); Lawrence S. Crossett, Pittsburgh, PA (US)

(73) Assignee: DEPUY (IRELAND) (IE)

( * ) Notice: Subject to any disclaimer, the term of this patent is extended or adjusted under 35 U.S.C. 154(b) by 221 days.

(21) Appl. No.: 13/801,329

(22) Filed: Mar. 13, 2013

(65) Prior Publication Data

US 2014/0276857 A1    Sep. 18, 2014

(51) Int. Cl.
*A61B 17/17* (2006.01)
*A61F 2/38* (2006.01)
*A61F 2/46* (2006.01)
*A61F 2/30* (2006.01)

(52) U.S. Cl.
CPC ........... *A61F 2/3868* (2013.01); *A61B 17/1764* (2013.01); *A61F 2/4684* (2013.01); *A61B 17/1717* (2013.01); *A61F 2/389* (2013.01); *A61F 2002/30553* (2013.01)

(58) Field of Classification Search
CPC ................................................... A61B 17/1764
See application file for complete search history.

(56) References Cited

U.S. PATENT DOCUMENTS

| | | | |
|---|---|---|---|
| 5,613,970 A | 3/1997 | Houston et al. | |
| 5,634,927 A | 6/1997 | Houston et al. | |
| 6,063,091 A | 5/2000 | Lombardo et al. | |
| 6,355,045 B1 | 3/2002 | Gundlapalli et al. | |
| 7,025,788 B2 | 4/2006 | Metzger et al. | |
| 7,153,326 B1 | 12/2006 | Metzger | |
| 7,867,234 B2 | 1/2011 | Collazo | |
| 7,959,639 B1 | 6/2011 | McGovern et al. | |
| 8,187,280 B2 | 5/2012 | May et al. | |
| 8,287,547 B2 | 10/2012 | Martin et al. | |
| 8,491,587 B2 | 7/2013 | McGovern et al. | |
| 2002/0120340 A1 | 8/2002 | Metzger et al. | |
| 2005/0154470 A1 | 7/2005 | Sekel | |
| 2008/0306603 A1 | 12/2008 | Reich et al. | |
| 2009/0125114 A1* | 5/2009 | May et al. .................. | 623/20.14 |

(Continued)

FOREIGN PATENT DOCUMENTS

EP            0 993 807 A1    4/2000

OTHER PUBLICATIONS

Zimmer NexGen LCCK, Surgical Technique for use with LCCK 4-in-1 Instrument, 2009, 52 pages.

(Continued)

*Primary Examiner* — David Bates
(74) *Attorney, Agent, or Firm* — Barnes & Thornburg, LLP

(57) ABSTRACT

Methods of surgically preparing a patient's tibia are disclosed. Some methods include positioning a guide tower on a surgically-prepared proximal surface above an opening of a medullary canal of the patient's tibia, attaching a stem trial to a lower end of an offset tool that is sized to be received in the guide tower, and advancing the stem trial through the guide tower and the surgically-prepared proximal surface into the medullary canal. The method may include moving the guide tower to a desired offset orientation on the surgically-prepared proximal surface and advancing a reamer through the guide tower into the medullary canal. The method may also include positioning a tibial base trial on the surgically-prepared proximal surface based on the desired offset orientation.

19 Claims, 24 Drawing Sheets

(56) References Cited

U.S. PATENT DOCUMENTS

| | | |
|---|---|---|
| 2009/0149964 A1 | 6/2009 | May et al. |
| 2009/0306787 A1 | 12/2009 | Crabtree et al. |
| 2012/0310246 A1 | 12/2012 | Belcher et al. |
| 2013/0325014 A1 | 12/2013 | Sordelet et al. |
| 2013/0325016 A1 | 12/2013 | Sordelet et al. |
| 2013/0325018 A1 | 12/2013 | Thomas et al. |
| 2013/0325019 A1 | 12/2013 | Thomas et al. |
| 2013/0325021 A1 | 12/2013 | Sordelet et al. |
| 2013/0325136 A1 | 12/2013 | Thomas et al. |
| 2014/0276837 A1 | 9/2014 | Chaney et al. |
| 2014/0276857 A1 | 9/2014 | Major |
| 2014/0276858 A1 | 9/2014 | Major et al. |
| 2014/0277546 A1 | 9/2014 | Major et al. |

OTHER PUBLICATIONS

DePuy Orthopaedics, Inc., Sigma Revision and M.B.T. Revision Tray, Surgical Technique, 2008, 82 pages.

Smith & Nephew, Legion, Revision Knee System, Surgical Technique, 2005, 40 pages.

Biomet, Vanguard SSK, Revision System, Surgical Technique, Feb. 2008, 64 pages.

GMK Revision, Surgical Technique, Ref. 99.27.12US rev. 1, Dec. 27, 1999, 74 pages.

PFC Sigma RP-F, Specialist 2 Instruments, Surgical Technique, Performance in Flexion, 2007, 32 pages.

P.F.C. Sigma Rotating Platform Knee System with M.B.T Tray, Primary Procedure with a Curved or Posterior Stablised Implant, 2003, 43 pages.

LCS High Performance Instruments, Surgical Technique, 2008, 44 pages.

Sigma High Performance Instruments, Design Rationale, 2007, 12 pages.

Sigma High Performance Instruments, Classic Surgical Technique, 2010, 52 pages.

Attune Knee System Surgical Technique, 2013, 73 pages.

\* cited by examiner

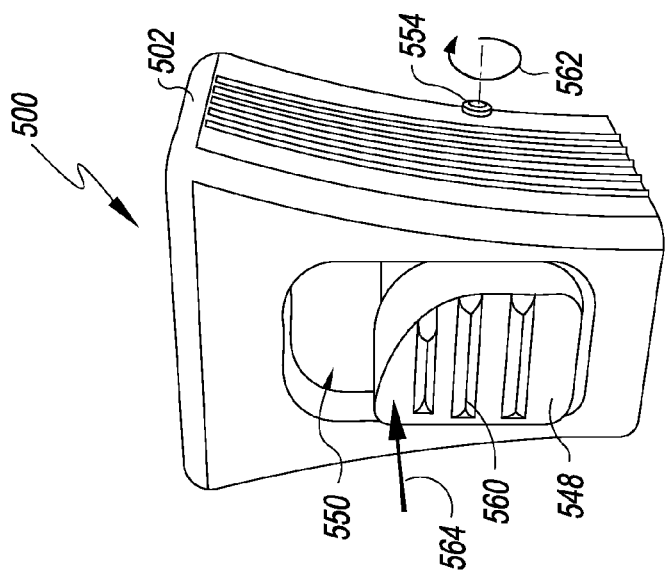
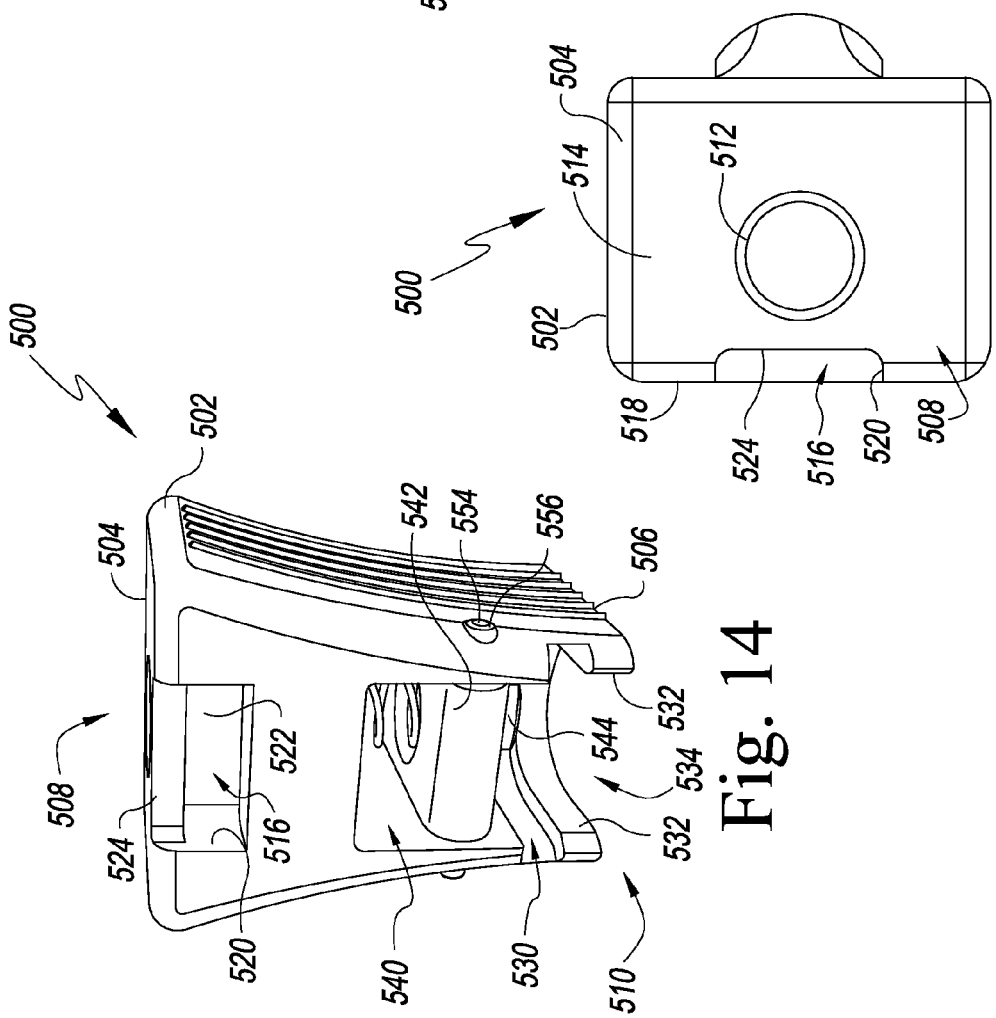
Fig. 16
Fig. 15
Fig. 14

METHOD OF SURGICALLY PREPARING A PATIENT'S TIBIA

CROSS-REFERENCE

Cross reference is made to copending U.S. patent application Ser. No. 13/801,352, which was filed on Mar. 13, 2013, entitled "TIBIAL ORTHOPAEDIC SURGICAL INSTRUMENTS FOR SETTING OFFSET"; and copending U.S. patent application Ser. No. 13/801,370, which was filed on Mar. 13, 2013, entitled "TIBIAL TRIAL INSTRUMENTS FOR SETTING OFFSET" and issued as U.S. Pat. No. 9,107,757 on Aug. 18, 2015, each of which is assigned to the same assignee as the present application, each of which is filed concurrently herewith, and each of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, sometimes called a "primary knee prosthesis," is surgically removed and a replacement or revision knee prosthesis is implanted. In some revision knee surgeries, all of the components of the primary knee prosthesis, including, for example, the tibial tray, the femoral component, and the polymer bearing, may be surgically removed and replaced with revision prosthetic components. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

According to one aspect of the disclosure, a method of surgically preparing a patient's tibia is disclosed. The method includes positioning a guide tower on a surgically-prepared proximal surface above an opening of a medullary canal of the patient's tibia, attaching a stem trial to a lower end of an offset tool that is sized to be received in the guide tower, and advancing the stem trial through the guide tower and the surgically-prepared proximal surface into the medullary canal. The method also includes rotating the offset tool to move the guide tower to a desired offset orientation on the surgically-prepared proximal surface, securing the guide tower to the patient's tibia at the desired offset orientation, removing the offset tool and the stem trial from the patient's tibia, advancing a reamer through the guide tower into the medullary canal, and positioning a tibial base trial on the surgically-prepared proximal surface based on the desired offset orientation.

In some embodiments, the method may also include attaching the stem trial to a stem adaptor, and securing the stem adaptor to the tibial base trial. Additionally, positioning the tibial base trial on the surgically-prepared proximal surface may include inserting the stem adaptor and the stem trial into the medullary canal.

In some embodiments, the method may include identifying a first offset indicator on the guide tower and the offset tool when the guide tower is in the desired offset orientation, and identifying a second offset indicator on the stem adaptor corresponding to the first offset indicator, rotating a first adaptor body of the stem adaptor relative to a second adaptor body to a position associated with the second offset indicator, and securing the first adaptor body in the position relative to the second adaptor body before inserting the stem adaptor and the stem trial into the medullary canal.

In some embodiments, the first adaptor body may define a first axis, the second adaptor body may define a second axis, and moving the tibial base trial on the surgically-prepared proximal surface may include moving the first axis in a circular path about the second axis.

Additionally, securing the stem adaptor to the tibial base trial and securing the first adaptor body in the position relative to the second adaptor body may in some embodiments include advancing a threaded shaft pivotally coupled to the tibial base trial into a threaded aperture of the stem adaptor. In some embodiments, rotating the offset tool to move the guide tower to the desired offset orientation may include moving the guide tower in a circular path. In some embodiments, the guide tower may define a first axis, the stem trial may define a second axis, and rotating the offset tool to move the guide tower on the surgically-prepared proximal surface of the patient's tibia may include moving the first axis in a circular path about the second axis.

In some embodiments, the method may include inserting a keel punch through a slot defined in the tibial base trial into the surgically-prepared proximal surface of the patient's tibia. Additionally, in some embodiments, the method may include positioning a tibial bearing trial over a lug of formed on the keel punch on the tibial base trial.

According to another aspect, the method of surgically preparing a patient's tibia includes positioning a guide tower on a surgically-prepared proximal surface above an opening of a medullary canal of the patient's tibia, the guide tower defining a first axis, attaching a stem trial to a lower end of an offset tool that is sized to be received in the guide tower, and advancing the stem trial through the guide tower and the surgically-prepared proximal surface into the medullary canal. The stem trial defines a second axis parallel to the first axis of the guide tower. The method also includes rotating the offset tool in the guide tower to move the guide tower on the surgically-prepared proximal surface such that the first axis is moved in a circular path about the second axis, identifying a desired offset orientation of the guide tower, adjusting a stem adaptor based on the desired offset orientation, securing the stem trial to the stem adaptor, inserting the stem adaptor and the stem trial into the medullary canal, and engaging the surgically-prepared proximal surface with a tibial base trial secured to the stem adaptor.

In some embodiments, adjusting the stem adaptor may include rotating a first adaptor body relative to a second adaptor body. In some embodiments, identifying the desired offset orientation of the guide tower may include identifying a first offset indicator corresponding to the desired offset orientation, and adjusting the stem adaptor may include identifying a second offset indicator on the stem adaptor corresponding to the desired offset orientation. Additionally, rotating the first adaptor body relative to the second adaptor body may include moving the first adaptor body to a rotational position associated with the second offset indicator.

In some embodiments, the method may include evaluating tibial base trial on the surgically-prepared proximal surface of the patient's tibia, and rotating the first adaptor body relative to the second adaptor body to move the tibial base trial on the surgically-prepared proximal surface of the patient's tibia.

The method also may include in some embodiments inserting a keel punch through a slot defined in the tibial base trial into the surgically-prepared proximal surface of the patient's tibia. Additionally, inserting the keel punch through the slot defined in the tibial base trial and into the surgically-prepared proximal surface of the patient's tibia may include inserting a portion of the keel punch into a slot defined in the stem adaptor.

According to another aspect, a method of performing an orthopaedic surgical procedure on a patient's tibia is disclosed. The method includes securing a stem trial to a stem adaptor, advancing a fastener secured to a tibial base trial into a threaded aperture of the stem adaptor such that the stem adaptor is secured to the tibial base trial, rotating a first adaptor body of the stem adaptor relative to a second adaptor body of the stem adaptor to position the stem adaptor in a desired offset orientation, advancing the fastener deeper into the threaded aperture to lock the first adaptor body and the second adaptor body in the desired offset orientation, inserting the stem adaptor and the stem trial through a surgically-prepared proximal surface of the patient's tibia into a medullary canal of the patient's tibia, and engaging the tibial base trial with the surgically-prepared proximal surface.

In some embodiments, the method may include positioning a base plate on the surgically-prepared proximal surface. The base plate may include a plurality of surface sections shaped to match surfaces of a prosthetic tibial tray. In some embodiments, the method may include advancing an offset tool through an opening in the base plate, and rotating the offset tool to move the base plate on the surgically-prepared proximal surface to determine the desired offset orientation.

Additionally, rotating the offset tool to move the base plate comprises may include identifying a first offset indicator corresponding to the desired offset orientation, and rotating the first adaptor body of the stem adaptor relative to the second adaptor body may include identifying a second offset indicator on the stem adaptor corresponding to the desired offset orientation.

In some embodiments, the method may include inserting a keel punch through a slot defined in the tibial base trial into the surgically-prepared proximal surface of the patient's tibia. The method may also include positioning a tibial bearing trial over a lug of formed on the keel punch on the tibial base trial.

According to one aspect of the disclosure, an orthopaedic surgical instrument assembly is disclosed. The instrument assembly includes a guide tower including a base surface adapted to be positioned on a proximal end of a patient's tibia. The guide tower also has a passageway that defines a first axis and extends through an opening defined in the base surface. The instrument assembly also includes an offset tool having a tool body including a lower end positioned in the passageway of the guide tower and a shaft attached to and extending from a lower surface of the tool body. The tool body is configured to rotate relative to the guide tower, and the shaft extends outwardly through the opening defined in the base surface and defines a second axis extending parallel to the first axis. When the orthopaedic surgical instrument assembly is viewed in a transverse plane and the shaft is rotated about the second axis, the tool body is rotated relative to the guide tower and the first axis of the guide tower is moved in a circular path about the second axis.

In some embodiments, the orthopaedic surgical instrument assembly may include a stem trial including an elongated body shaped to be positioned in an intramedullary canal of the patient's tibia. In some embodiments, the stem trial may have an externally-threaded upper end, and the shaft may have an internally-threaded lower end that receives the externally-threaded upper end of the stem trial.

In some embodiments, the tool body may be configured to rotate 360 degrees relative to the guide tower. Additionally, the guide tower may include a cylindrical inner wall that defines the passageway and is substantially smooth. The tool body may include an outer wall that engages the cylindrical inner wall of the guide tower. The outer wall may have a groove defined therein.

In some embodiments, the tool body may be configured to move in a first direction along the first axis between a first position in which the lower end of the tool body is removed from the passageway and a second position in which the lower end of the tool body is positioned in the passageway.

In some embodiments, the offset tool may include a flange that extends outwardly from an upper end of the tool body and engages an upper end of the guide tower to prevent the tool body from moving in the first direction beyond the second position.

Additionally, in some embodiments, the instrument assembly may include a reamer having a plurality of cutting flutes. The reamer may be configured to be positioned in the passageway when the tool body is removed from the passageway.

In some embodiments, the guide tower may include a base plate including the base surface, an upper surface positioned opposite the base surface, and an outer wall extending between the base surface and the upper surface. The outer wall may include a convex curved anterior section and a concave curved posterior section shaped to match the convex curved anterior section and the concave curved posterior section of a prosthetic tibial tray. The guide tower may also include a housing extending upwardly from the upper surface of the base plate. The housing may have the passageway extending therethrough. A plurality of guide pin holes may extend through the upper surface and the base surface of the base plate.

In some embodiments, the instrument assembly may include an indicator configured to indicate a position of the first axis on the circular path. Additionally, the indicator may include a first marking formed on an upper end of the guide tower, and a plurality of second markings formed on the offset tool. Each second marking may correspond to a position of the first axis on the circular path. In some embodiments, each second marking may include a numerical marking indicative of the position of the second axis on the circular path.

In some embodiments, the indicator may include a boss extending upwardly from an upper end of tool body, and a plurality of markings formed an upper end of the guide tower. Each second marking may correspond to the position of the first axis on the circular path. When a tip of the boss is aligned with one of the plurality of markings, the second marking may indicate the position of the first axis on the circular path.

In some embodiments, the offset tool may include a grip to rotate the tool body.

According to another aspect, an orthopaedic surgical instrument assembly includes a guide tower including a base surface adapted to be positioned on a proximal end of a patient's tibia. The guide tower has a passageway that defines a first axis. The instrument assembly also includes an offset tool including a tool body having a lower end removably positioned in the passageway of the guide tower, and a stem trial removably coupled to a lower end of the offset tool and extending parallel to the first axis. When the orthopaedic surgical instrument assembly is viewed in a transverse plane and the stem trial is rotated, the tool body is configured to rotate relative to the guide tower to move the guide tower in a circular path about the stem trial.

In some embodiments, the instrument assembly may include an indicator configured to indicate a position of the guide tower on the circular path. Additionally, the indicator may include a first marking formed on an upper end of the guide tower, and a plurality of second markings formed on the offset tool. Each second marking may correspond to a position of the guide tower on the circular path.

In some embodiments, the instrument assembly may also include a reamer configured to be positioned in the passageway. The reamer may have a plurality of cutting flutes and a longitudinal axis that is aligned with the first axis when the reamer is positioned in the passageway.

According to another aspect, an orthopaedic surgical instrument assembly includes a guide tower including a base surface adapted to be positioned on a proximal end of a patient's tibia and defining a first axis extending through the base surface and an offset tool attached to the guide tower and configured to rotate about the first axis. The offset tool includes a tool body that is positioned in the guide tower and integrally formed with a shaft extending through an opening defined in the base surface of the guide tower. The instrument assembly also includes a stem trial removably coupled to a lower end of the shaft. The stem trial cooperates with the shaft to define a second axis extending parallel to the first axis. When the orthopaedic surgical instrument assembly is viewed in a transverse plane and the stem trial is rotated about the second axis, the offset tool is configured to rotate about the first axis to move the guide tower about the second axis.

In some embodiments, the guide tower may include a base plate including the base surface, an upper surface positioned opposite the base surface, and an outer wall extending between the base surface and the upper surface. The guide tower may also include a housing extending upwardly from the upper surface of the base plate. The housing may receive the offset tool. A plurality of guide pin holes may extend through the upper surface and the base surface of the base plate.

According to another aspect, an orthopaedic surgical instrument assembly includes a tibial bearing trial including an articulation surface and a bottom surface opposite the articulation surface and a tibial base trial adapted to be positioned on a surgically-prepared proximal end of a patient's tibia. The tibial base trial includes an upper surface engaged with the bottom surface of the tibial bearing trial. A base fastener is attached to the tibial base trial, and the base fastener includes a shaft configured to rotate relative to the tibial base trial. The instrument assembly also includes a stem adaptor secured to the shaft of the base fastener. The stem adaptor includes a first adaptor body engaged with a lower surface of the tibial base trial. The first adaptor body also defines a first axis. The stem adaptor also includes a second adaptor body pivotally coupled to the first adaptor body. The second adaptor body defines a second axis extending parallel to the first axis. When the second adaptor body is in a fixed position, the first adaptor body is configured to pivot relative to the second adaptor body to move the first axis a circular path about the second axis.

In some embodiments, the instrument assembly may include a stem trial secured to the second adaptor body of the stem adaptor. The stem trial may include an elongated body shaped to be positioned in an intramedullary canal of the patient's tibia. In some embodiments, the stem trial may have an externally-threaded upper end. The second adaptor body may have an internally-threaded lower end that receives the externally-threaded upper end of the stem trial.

In some embodiments, the first adaptor body may be configured to rotate 360 degrees relative to the second adaptor body. In some embodiments, the stem adaptor may include an adaptor fastener to secure the first adaptor body to the second adaptor body. Additionally, the adaptor fastener may include a lug having a lower end extending through an opening defined in a lower wall of the first adaptor body and an annular flange sized to prevent an upper end of the lug from passing through the opening. The adaptor fastener may also include a pin securing the lug to the second adaptor body.

In some embodiments, the first adaptor body may have an opening defined in an upper surface thereof and a passageway extending downwardly from the opening to the lower wall, and the annular flange of the lug may be positioned in the passageway. Additionally, in some embodiments, the lug may be movable along the first axis between a first position in which the first adaptor body is permitted to pivot relative to the second adaptor body, and a second position in which the first adaptor body is prevented from pivoting relative to the second adaptor body.

In some embodiments, an upper edge of the second adaptor body may engage an annular flange of the first adaptor body when the lug is in the second position to prevent the first adaptor body from pivoting relative to the second adaptor body.

In some embodiments, the lug may have a threaded aperture defined in the upper end thereof, and the shaft of the base fastener may be positioned in the passageway defined in the first adaptor body. The shaft may include a threaded end that is received in the threaded aperture of the lug. When the shaft is rotated in a first direction, the lug may be moved in an upward direction along the first axis toward the second position, and when the shaft is rotated in a second direction opposite the first direction, the lug may be moved in a downward direction along the first axis toward the first position.

In some embodiments, the base fastener may include a button head and a sleeve secured to the shaft below a lower surface of the tibial base trial. The tibial base trial may be retained between the button head and the sleeve of the base fastener.

In some embodiments, the instrument assembly may include a base insert removably coupled to the tibial base trial having a first arm and a second arm extending below the lower surface of the tibial base trial. The first arm and the second arm may be received in and extend outwardly from a slot defined in the first adaptor body.

According to another aspect, an orthopaedic surgical instrument assembly includes a tibial base trial adapted to be positioned on a surgically-prepared proximal end of a patient's tibia. The tibial base trial includes an upper surface, a lower surface positioned opposite the upper surface, a convex curved anterior surface extending between the upper surface and the lower surface and a concave posterior surface extending between the upper surface and the lower surface. The instrument assembly includes a base fastener including a button head positioned above the upper surface of the tibial base trial, a shaft extending downwardly from the button head through the tibial base trial, and a sleeve secured to the shaft below the lower surface of the tibial base trial such the tibial base trial is retained between the button head and the sleeve of the base fastener. A stem adaptor is secured to the shaft of the base fastener, and the stem adaptor includes a first adaptor body engaged with a lower surface of the tibial base trial that defines a first axis and a second adaptor body pivotally coupled to the first adaptor body and defining a second axis offset from the first axis. A stem trial is removably coupled to the second adaptor body of the stem adaptor.

In some embodiments, the stem adaptor may include a locking mechanism configured to prevent the first adaptor body from pivoting relative to the second adaptor body. In some embodiments, the locking mechanism may include a lug extending through an opening defined in the first adaptor body. The lug may be moveable along the first axis between a first position in which the first adaptor body is permitted to pivot relative to the second adaptor body and a second position in which the first adaptor body is prevented from pivoting relative to the second adaptor body.

In some embodiments, a lower end of the lug may be secured to the second adaptor body such that the second adaptor body is moved with the lug along the first axis. In some embodiments, the second adaptor body may include an aperture defined in an upper end thereof, and the first adaptor body may have a lower end positioned in the aperture defined in the second adaptor body.

According to another aspect, an orthopaedic surgical instrument assembly includes a tibial bearing surface trial including an articulation surface, a shim secured to the tibial bearing surface trial, and a tibial base trial adapted to be positioned on a surgically-prepared proximal end of a patient's tibia. The tibial base trial includes an upper surface engaged with a bottom surface of the shim. The instrument assembly also includes a base fastener including a button head, a shaft extending downwardly from the button head through the tibial base trial, and a sleeve secured to the shaft below the lower surface of the tibial base trial such the tibial base trial is retained between the button head and the sleeve of the base fastener. The instrument assembly further includes a stem adaptor secured to the shaft of the base fastener. The stem adaptor includes a first adaptor body that defines a first axis engaged with a lower surface of the tibial base trial, and a second adaptor body that defines a second axis offset from the first axis and pivotally coupled to the first adaptor body. A stem trial is removably coupled to the second adaptor body of the stem adaptor.

In some embodiments, the instrument assembly includes a removal tool configured to be secured to the button head of the base fastener.

BRIEF DESCRIPTION OF THE DRAWINGS

The detailed description particularly refers to the following figures, in which:

FIG. 14 is a perspective view of a removal tool;

FIG. 15 is a top plan view of the removal tool of FIG. 14;

FIG. 16 is a perspective view of the removal tool of FIGS. 14-15;

DETAILED DESCRIPTION OF THE DRAWINGS

Figure 1:
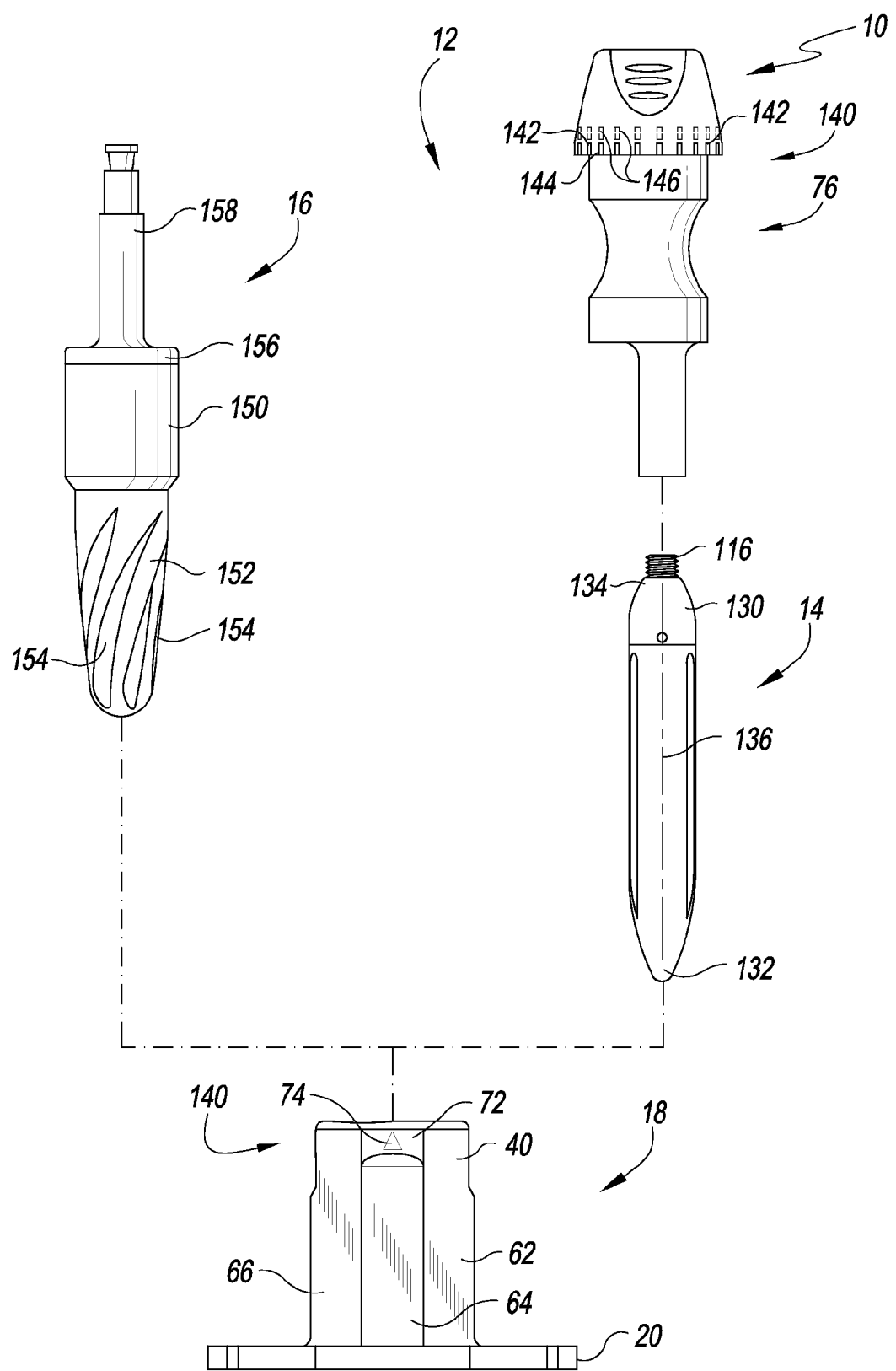
FIG. 1 is an exploded perspective view of a group of orthopaedic surgical instruments of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a group of orthopaedic surgical instruments of an orthopaedic surgical instrument system 10 (hereinafter instrument system 10) is shown. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses, such as, for example, the revision tibial prosthesis 600 shown in FIG. 19, which are surgically implanted in the body of the patient.

The instrument system 10 includes an offset guide instrument assembly 12 and a stem trial 14 configured to be attached to the offset guide instrument assembly 12. As described in greater detail below, the stem trial 14 is configured to be positioned in the medullary canal of the patient's tibia during the orthopaedic surgical procedure. The offset guide instrument assembly 12 and the stem trial 14 are configured to identify a desired offset orientation of the revision tibial prosthesis 600. The offset guide instrument assembly 12 may be used to guide a surgical reamer 16 during a reaming operation of the proximal end of the patient's tibia, as described in greater detail below.

In the illustrative embodiment, the offset guide instrument assembly 12, the stem trial 14, and the reamer 16 are formed from metallic materials such as, for example, stainless steel or cobalt chromium. It should be appreciated that in other embodiments some of the instruments of system 10 may be formed from a polymeric material such as plastic. For example, the stem trial 14 may be formed from a rigid plastic material while the reamer 16 may be formed partially from plastic overmolded on a metallic material.

Figure 2:
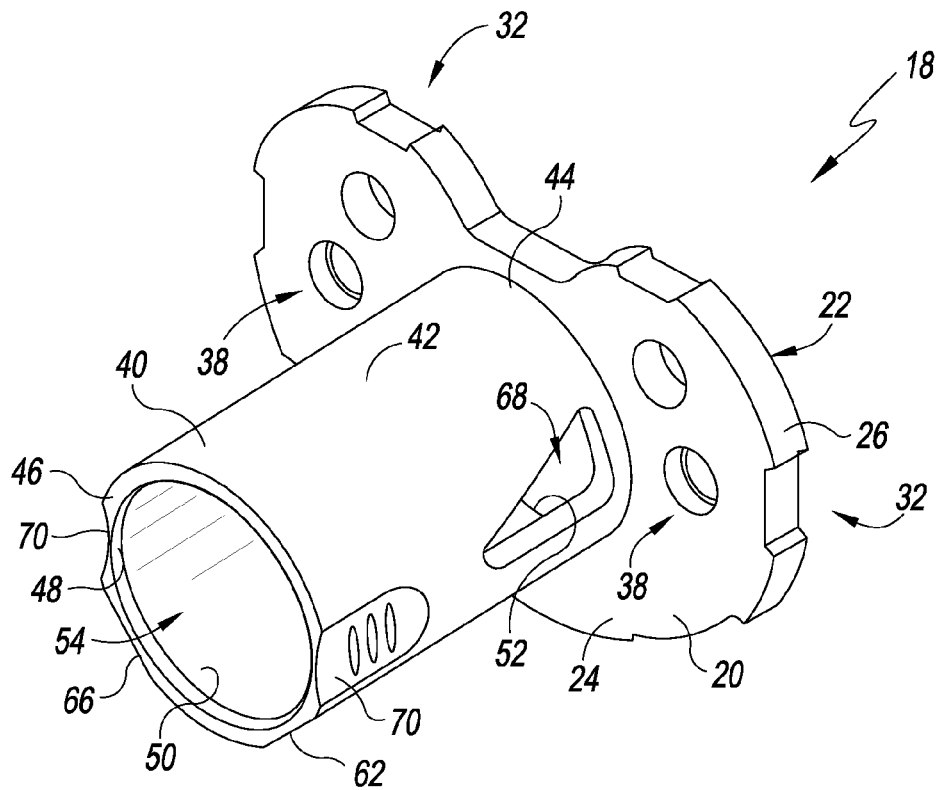
FIG. 2 is a perspective view of a guide tower of the instrument group of FIG. 1.
Figure 3:
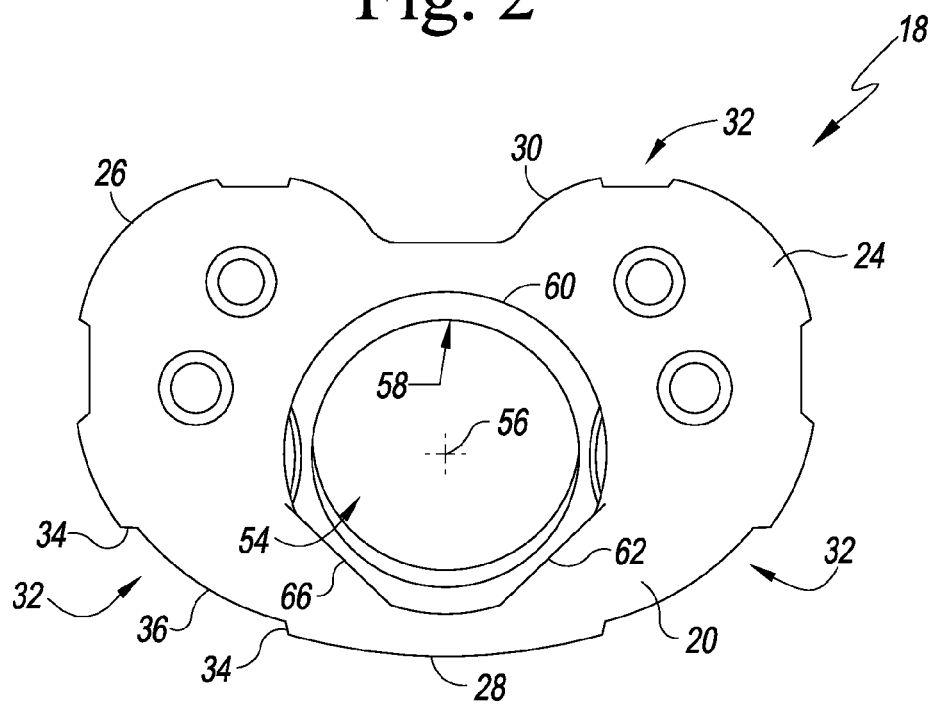
FIG. 3 is a top plan view of the guide tower of FIG. 2.

The offset guide instrument assembly 12 includes a guide tower 18 configured to be positioned on a proximal end of a patient's tibia. As shown in FIGS. 2 and 3, the guide tower 18 includes a base plate 20 shaped to be positioned on a proximal end of a patient's tibia. The base plate 20 has a bottom surface 22, a top surface 24 positioned opposite the bottom surface 22, and an outer wall 26 extending between the surfaces 22, 24. The outer wall 26 has an anterior section 28 shaped to match a section of a prosthetic tibial tray 602 of the prosthesis 600 and a posterior section 30 also shaped to match a section of the prosthetic tibial tray 602. In the illustrative embodiment, the anterior section 28 of the outer wall 26 is convexly curved to match an anterior section 618 of the prosthetic tibial tray 602 (see FIG. 19), and the posterior section 30 is concave to match a posterior section 620 of the prosthetic tibial tray 602.

In the illustrative embodiment, a plurality of slots 32 are defined in the outer wall 26 of the base plate 20. Each slot 32 is defined by a pair of spaced apart edge surfaces 34 and a connecting surface 36 extending between the edge surfaces 34. The connecting surfaces 36 of the slots 32 define a profile associated with one size of a prosthetic tibial tray 602, while the outer wall 26 defines another profile associated with a second, larger size prosthetic tibial tray 602. As such, one guide tower 18 may be used to evaluate more than one prosthetic tibial tray size. The slots 32 are arranged to correspond to anatomical landmarks that the surgeon may use to size the prosthetic tibial component and consider bone coverage. Those anatomical landmarks include the anterior-medial plateau and the medial/lateral width of the tibia. It should be appreciated that the guide tower 18 may be formed in a number of different sizes to accommodate patient's having different-sized bones.

A number of fastener holes 38 are defined in the base plate 20. As shown in FIG. 3, each fastener hole 38 extends through the bottom surface 22 and the top surface 24 of the base plate 20. Each hole 38 is sized to receive a fastener such as, for example, a fixation or bone pin 724 (see FIG. 24), which may be utilized to secure the guide tower 18 to the proximal end of the patient's tibia, as described in greater detail below. In the illustrative embodiment, the base plate 20 includes two fastener holes 38; in other embodiments, the base plate 20 may include additional or fewer fastener holes.

As shown in FIG. 2, the guide tower 18 also includes a housing 40 secured to the base plate 20. The housing 40 includes an outer wall 42 extending upwardly from a lower end 44 attached to the top surface 24 of the base plate 20. In the illustrative embodiment, the housing 40 and the base plate 20 are formed as a single monolithic part. It should be appreciated that in other embodiments the housing 40 and the base plate 20 may be formed separately and later assembled to form the guide tower 18.

An opening 48 is defined in the upper end 46 of the housing 40, and an inner wall 50 extends downwardly from the opening 48. The inner wall 50 extends through the base plate 20 to an opening 52 defined in the bottom surface 22 of the base plate 20. As shown in FIGS. 2 and 3, the inner wall 50 defines a passageway 54 extending through the guide tower 18. The passageway 54 has a longitudinal axis 56, which extends into the patient's tibia when the guide tower 18 is positioned on the patient's tibia. In the illustrative embodiment, the inner wall 50 is substantially smooth and cylindrical; as a result, the passageway 54 is also substantially cylindrical and has an inner diameter 58.

The outer wall 42 of the housing 40 has a curved posterior surface 60 and a number of planar anterior surfaces 62, 64, 66. As shown in FIG. 2, a slot 68 is defined in the curved posterior surface 60 adjacent to the lower end 44 of the housing 40. The slot 68 extends through the entire thickness of housing 40—that is, through the outer wall 42 and the inner wall 50—and opens into the passageway 54. In the illustrative embodiment, the slot 68 is substantially triangular in shape. It should be appreciated that in other embodiments the slot 68 may be rectangular, square, or other geometric form. In the illustrative embodiment, the curved posterior surface 60 has another slot (not shown) defined on the opposite side of the housing 40 that has a configuration similar to the slot 68.

The curved posterior surface 60 of the outer wall 42 includes a pair of contoured sections 70 located at the upper end 46 of the housing 40. The contoured sections 70 are configured to be gripped by the surgeon or other user to position or support the guide tower 18 during use. As shown in FIG. 1, the housing 40 also includes a flange 72, which extends outwardly from the anterior surface 64 of the outer wall 42 at the upper end 46. As described in greater detail below, an indicator marking 74 is defined in the flange 72.

Figure 4:
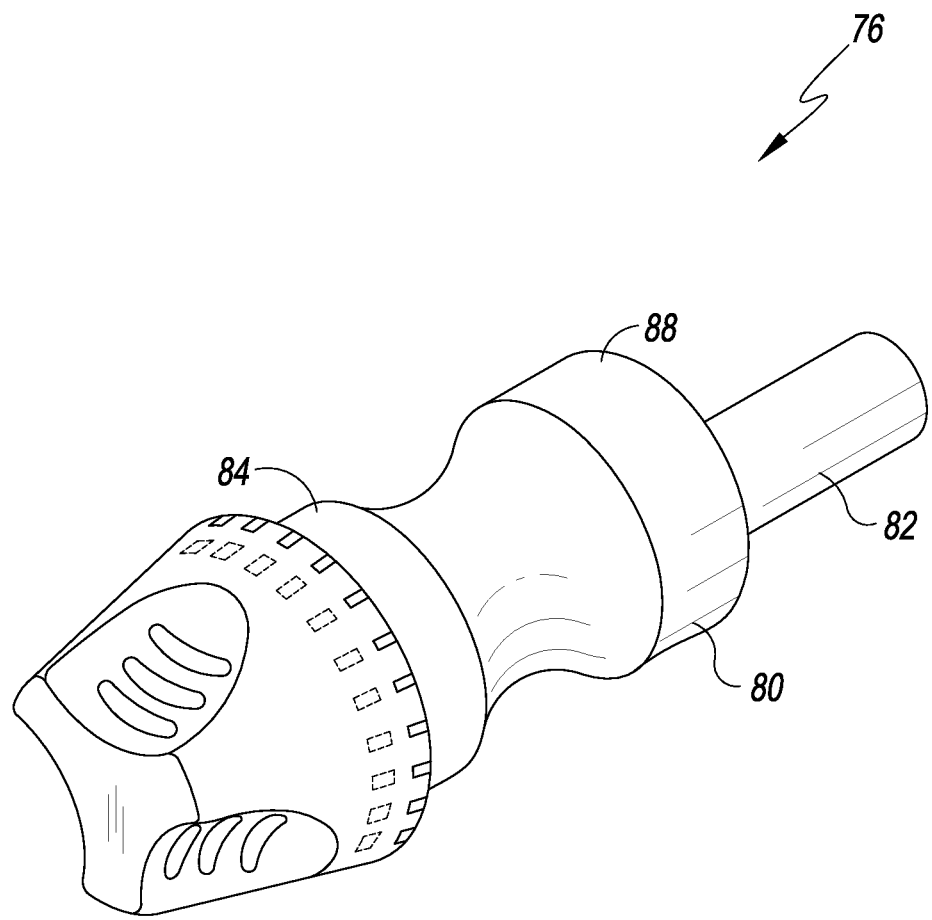
FIG. 4 is a perspective view of an offset guide tool of the instrument group of FIG. 1.
Figure 5:
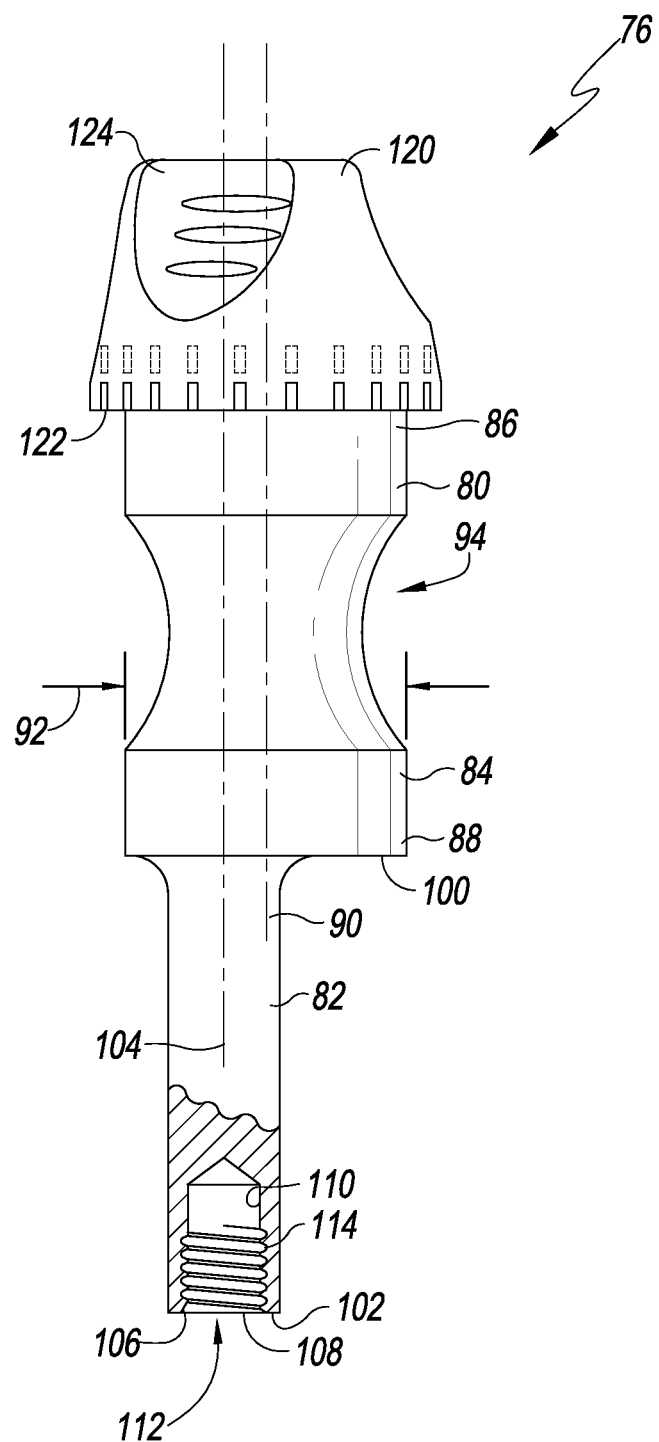
FIG. 5 is an elevation view of the offset guide tool of FIG. 4.

In addition to the guide tower 18, the offset guide instrument assembly 12 also includes an offset guide tool 76. As shown in FIGS. 4 and 5, the offset guide tool 76 has a barrel body 80 sized to be received in the passageway 54 of the guide tower 18 and a shaft 82 attached to the barrel body 80. As shown in FIG. 4, the barrel body 80 includes an outer wall 84 extending between an upper end 86 and a lower end 88. The barrel body 80 has a longitudinal axis 90 extending through the ends 86, 88. The outer wall 84 is cylindrical and has an outer diameter 92 that is less than or equal to the inner diameter 58 of the passageway 54 of the housing 40.

In that way, the outer wall 84 of the barrel body 80 is shaped to be received in the passageway 54 of the housing 40. In use, a surgeon or other user may rotate the offset guide tool 76 relative to the guide tower 18 when the barrel body 80 is positioned in the passageway 54. Additionally, the longitudinal axis 90 of the barrel body 80 is coincident with the longitudinal axis 56 of the passageway 54 when the offset guide tool 76 is attached to the tower 18.

In the illustrative embodiment, a groove 94 is defined in the outer wall 84. As shown in FIG. 5, the groove 94 has an hour-glass shape. It should be appreciated that in other embodiments the groove 94 may be omitted or have a different geometric shape.

As described above, the offset guide tool 76 also includes a shaft 82 attached to the barrel body 80. As shown in FIG. 5, the shaft 82 extends downwardly from a bottom surface 100 of the barrel body 80 to a lower end 102. When the barrel body 80 is positioned in the passageway 54 of the guide tower 18, the lower end 102 of the shaft 82 extends outwardly from the passageway 54 and is positioned below the bottom surface 22 of the base plate 20. In the illustrative embodiment, the shaft 82 is substantially cylindrical and has a longitudinal axis 104 offset from and extending parallel to the longitudinal axis 90 of the barrel body 80. In the illustrative embodiment, the longitudinal axis 104 is offset from the longitudinal axis 90 by approximately four millimeters. It should be appreciated that in other embodiments the offset may be greater than zero and less than four millimeters. In still other embodiments, the offset may be greater than four millimeters. When the barrel body 80 is positioned in the passageway 54 of the guide tower 18, the longitudinal axis 104 is also offset from the longitudinal axis 56, which, as described above, is coincident with the axis 90 of the barrel body 80.

As shown in FIG. 5, the shaft 82 has an opening 106 defined in the end surface 108 thereof. An inner wall 110 extends upwardly from the opening 106 to define an aperture 112 in the lower end 102 of the shaft 82. The inner wall 110 has a plurality of internal threads 114 formed thereon. As described in greater detail below, the threads 114 are configured to engage a plurality of external threads 116 (see FIG. 1) of the stem trial 14 to secure the stem trial 14 to the offset guide tool 76.

The offset guide tool 76 also includes a knob 120 attached to the upper end 86 of the barrel body 80. As shown in FIG. 5, the knob 120 includes an annular flange 122 extending from the upper end 86 of the barrel body 80. The flange 122 is sized to engage the housing 40 of the guide tower 18, as described in greater detail below. The knob 120 also includes a contoured outer surface 124, which may be gripped by the surgeon or other user to rotate the offset guide tool 76 when the barrel body 80 is received in the guide tower 18.

In the illustrative embodiment, the barrel body 80, the shaft 82, and knob 120 are formed as a single monolithic component. It should be appreciated that in other embodiments the barrel body 80, the shaft 82, and knob 120 may be formed separately and later assembled to form the offset guide tool 76. For example, in other embodiments, the knob 120 may be formed separately from a plastic material while the barrel body 80 and the shaft 82 are formed as a single monolithic part.

As described above, the system 10 also includes a stem trial 14, which is configured to be secured to the offset guide instrument assembly 12. As shown in FIG. 1, the stem trial 14 has an elongated body 130 that extends from a tip 132 to an upper end 134. The upper end 134 is sized to be received in the aperture 112 defined in the shaft 82 and has a plurality of external threads 116 that correspond to the internal threads 114 lining the aperture 112. In that way, the stem trial 14 may be threaded onto the shaft 82 to secure the trial 14 to the offset tool 76. In other embodiments, the stem trial may be internally-threaded and the shaft externally-threaded. Additionally, it should be appreciated that in other embodiments the stem trial 14 may be secured to the shaft 82 of the offset tool 76 via a taper fit, press fit, or other fastening arrangements. It should be appreciated that other stem trials having different configurations may be provided. For example, the outer diameter and/or length of the stem trial may vary to permit the surgeon to trial or test prosthetic stem components of different sizes, as described in greater detail below. The elongated body 130 has a longitudinal axis 136 that is coincident with the axis 104 of the shaft 82 when the stem trial 14 is secured to the offset tool 76.

As described above, the base plate 20 of the guide tower 18 includes an anterior section 28 and a posterior section 30 that are shaped to match the profile of the prosthetic tibial tray 602, and the stem trial 14 is shaped to match the configuration of the elongated body 634 of a prosthetic tibial stem component 612 (see FIG. 19) securable to the component 602. Similarly, the offset of the longitudinal axis 136 of the stem trial 14 from the axis 90 of the guide tower 18 is the same as the offset of the prosthetic tibial stem component 612 from the prosthetic tibial tray 602. Consequently, the offset guide instrument assembly 12 may be used to identify a planned offset orientation of the prosthetic tibial stem component 612 and the prosthetic tibial tray 602 that provides maximum coverage of the surgically-prepared proximal surface prior to reaming the patient's bone.

To do so, the guide tower 18 may be positioned on the proximal end of the patient's tibia. The stem trial 14 may be secured to the shaft 82 of the offset guide tool 76. The stem trial 14 and the barrel body 80 of the offset guide tool 76 may then be advanced through the passageway 54 of the guide tower 18 to position the stem trial 14 in the medullary canal of the patient's tibia. With the stem trial 14 positioned in the medullary canal, the offset guide tool 76 may be rotated within the guide tower 18 relative to the longitudinal axis 136 of the stem trial 14. As the tool 76 is rotated, the guide tower 18 is moved along a circular path relative to the stem trial 14 between different offset orientations to identify a location on the surgically-prepared proximal surface of the patient's tibia providing maximum coverage.

As shown in FIG. 1, the offset guide instrument assembly 12 includes an offset indicator 140 configured to indicate the offset orientation between the stem trial 14 and the guide tower 18. In the illustrative embodiment, the offset indicator 140 includes a marking 74 defined on the guide tower 18 and a plurality of markings 142 defined on the knob 120 of the offset tool 76. As described in greater detail below, each marking 142 of the knob 120 corresponds to a different offset orientation. In the illustrative embodiment, the marking 74 is arrow-shaped, and the markings 142 on the knob 120 include lines 144 and numerical indicators 146, which are associated with the lines 144 to identify the offset orientations. When the marking 74 is aligned with one of the lines 144, the numerical indicator 146 corresponding to that line 144 may be read to determine the offset orientation. When the marking 74 is positioned between the lines 144, the surgeon may utilize the lines 144 and/or numerical indicators 146 to determine the offset orientation.

As described above, the system 10 also includes a surgical reamer 16. The surgical reamer 16 includes a cylindrical main body 150 and a conical cutting head 152 extending downwardly from the main body 150. As shown in FIG. 1, the cutting head 152 has a plurality of cutting teeth or flutes 154 configured to cut the patient's bone. The cylindrical main body 150 has a depth stop indicator 156, which, when aligned with the upper end 46 of the guide tower 18, identifies the maximum desired depth of the cutting head 152 into the patient's bone. The surgical reamer 16 also includes a shank 158 that extends upwardly from the main body 150. A surgical drill may engage the shank 158 to secure the reamer 16 to the drill for use during a surgical procedure.

Figure 6:
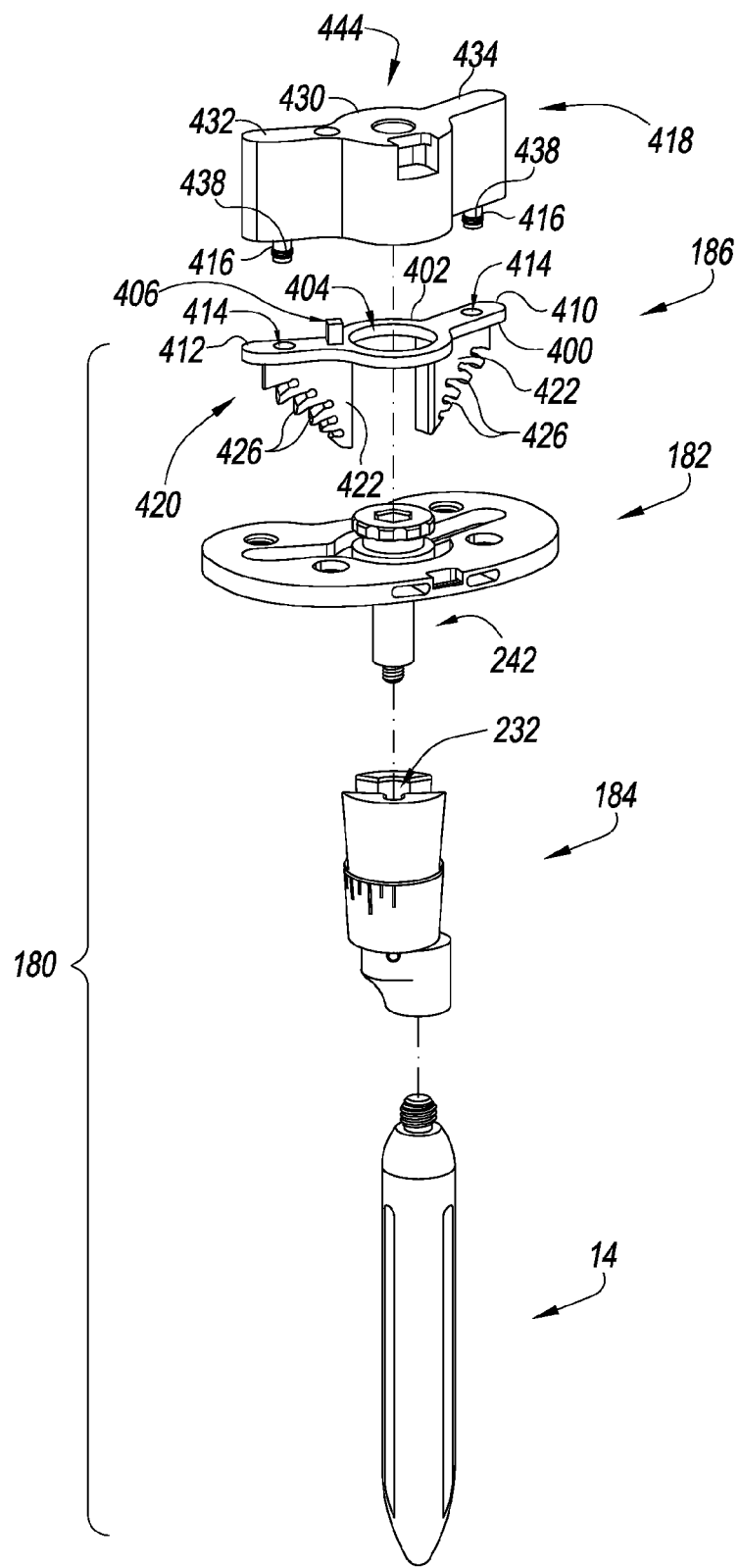
FIG. 6 is an exploded perspective view of a tibial trial assembly of the orthopaedic surgical instrument system.

Referring now to FIGS. 6-13, the orthopaedic surgical instrument system 10 also includes a tibial tray trial assembly 180 (see FIG. 6) and a number of tibial bearing trial assemblies 450 (see FIG. 13) that may be used to size and select the prosthetic components of a revision knee prosthesis 600. As shown in FIG. 6, the tibial tray trial assembly 180 includes a tibial base trial 182 and an offset stem adaptor 184 configured to be secured to the tibial base trial 182. The tibial tray trial assembly 180 also includes the stem trial 14, which may be secured to the offset adaptor 184, and a base insert 186 that may be attached to the tibial base trial 182. In the illustrative embodiment, each element of the tibial tray trial assembly 180 is formed from a metallic material, such as, for example, stainless steel or cobalt chromium.

Figure 7:
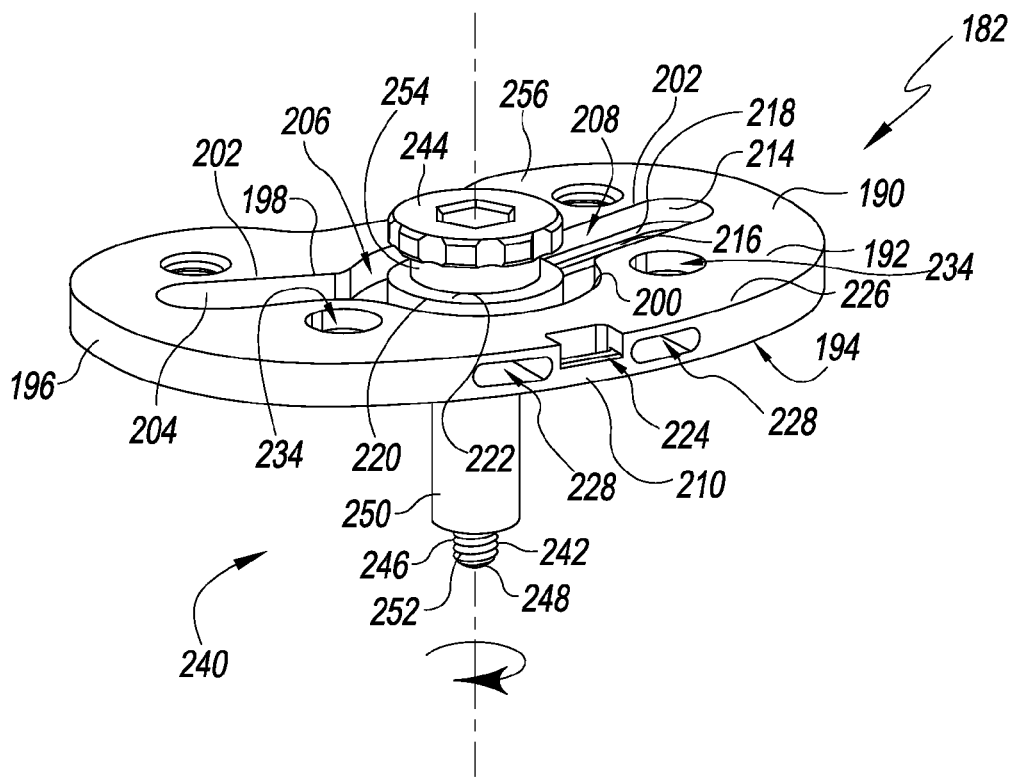
FIG. 7 is a perspective view of a tibial base trial of the tibial trial assembly of FIG. 6.
Figure 8:
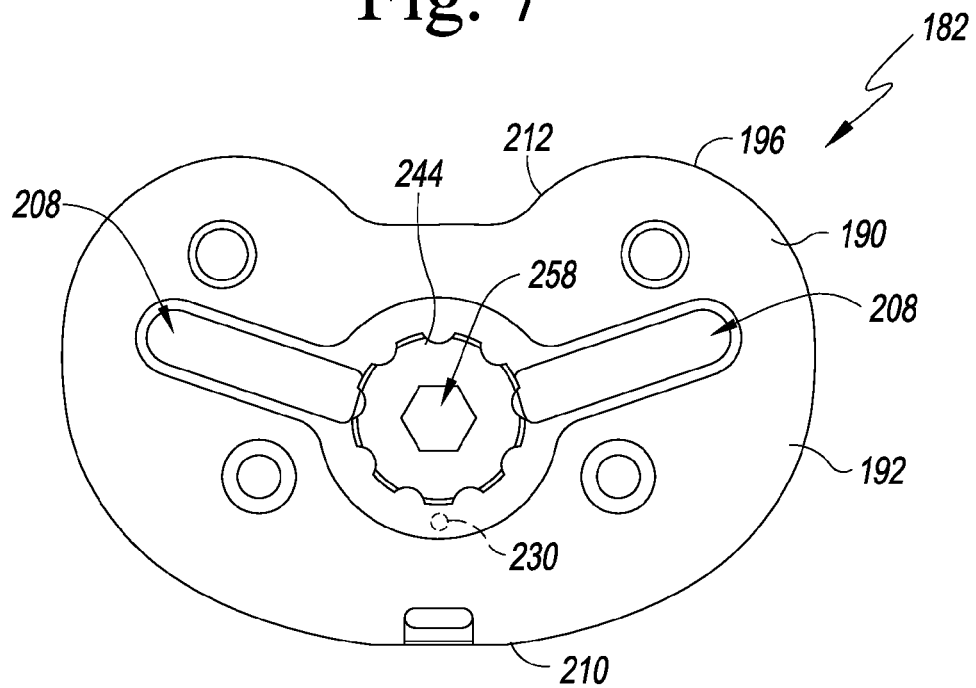
FIG. 8 is a top plan view of the tibial base trial of FIG. 7.

Referring now to FIGS. 7-8, the base trial 182 includes a plate 190 shaped to be positioned on a proximal end of a patient's tibia. The plate 190 has an upper surface 192, a lower surface 194, and an outer side wall 196 extending between the surfaces 192, 194. A plate opening 198 is defined in the upper surface 192, and the plate opening 198 includes a central opening 200 and a pair of elongated openings 202 extending outwardly therefrom. An inner wall 204 extends downwardly from the opening 198 to define a passageway 206 and a passageway 208 through the plate 190. As will be described in greater detail below, the configuration of the passageways 206, 208 permits the advancement of a keel punch and various other instruments into the proximal end of the patient's tibia.

The outer side wall 196 has an anterior section 210 shaped to match a section of the prosthetic tibial tray 602 and a posterior section 212 also shaped to match a section of the prosthetic tibial tray 602. In the illustrative embodiment, the anterior section 210 of the side wall 196 is convexly curved to match an anterior section 618 of the prosthetic tibial tray 602, and the posterior section 212 is concavely curved to match a posterior section 620 of the prosthetic tibial tray 602. As a result, the sections 210, 212 of the trial plate 190 is also shaped to match the sections 28, 30, respectively, of the base plate 20 of the guide tower 18. It should be appreciated that the tibial base trial 182 may be formed in a number of different sizes to accommodate tibias of various sizes.

The inner wall 204 of the trial plate 190 includes an upper wall 214 and a lower wall 216 offset or otherwise spaced inwardly from the upper wall 214. As shown in FIGS. 7-8, the walls 214, 216 cooperate to define a shelf surface 218 therebetween, and a platform 220 extends upwardly from the shelf surface 218. In the illustrative embodiment, the platform 220 is spaced apart from the upper wall 214 and has a top surface 222 that is co-planar with the upper surface 192 of the plate 190.

In the illustrative embodiment, the plate 190 also includes a lever-receiving notch 224 that is defined in an anterior aspect 226 thereof. As shown in FIG. 7, oblong-shaped apertures 228 are defined in the side wall 196 on each side of the notch 224. The notch 224 and the apertures 228 are configured to receive a lever and a pair of pins, respectively, associated with an alignment handle.

As shown in FIG. 8, the base trial 182 includes a pin 230, which extends downwardly from the lower surface 194 of the plate 190. As described in greater detail below, the pin 230 is sized to be received in a notch 232 defined in the offset adaptor 184. The plate 190 also includes a number of fastener guides 234. Each fastener guide 234 includes a bore 236 configured to receive a fastener such as a fixation pin, which may be utilized to secure the base trial 182 to the proximal end of the patient's tibia.

As shown in FIG. 7, the tibial base trial assembly 180 includes a locking mechanism 240 configured to secure the tibial base trial 182 to the offset adaptor 184. In the illustrative embodiment, the locking mechanism 240 includes a fastener 242 pivotally coupled to the tibial base trial 182. The fastener 242 is permanently secured to the plate 190 of the base trial 182, but it should be appreciated that in other embodiments the fastener may be removable from the tibial base trial or secured to the intramedullary orthopaedic surgical instruments.

The fastener 242 of the locking mechanism 240 includes a button head 244 positioned above the top surface 222 of the platform 220 and a central shaft 246 secured to the button head 244. The central shaft 246 extends through an opening (not shown) defined in the platform 220 to a lower end 248. An outer sleeve 250 is secured to the central shaft 246 between the lower end 248 and the lower surface 194 of the trial plate 190 such that the trial plate 190 is retained between the button head 244 and the sleeve 250. In that way, the fastener 242 may be secured to the base trial 182. As shown in FIG. 7, the fastener 242 includes a plurality of external threads 252, which are formed on the central shaft 246. The external threads 252 are configured to engage a plurality of internal threads 382 (see FIG. 10) of the offset adaptor 184 to secure the offset adaptor 184 to the base trial 182.

The button head 244 of the fastener 242 includes a neck 254, which confronts the platform 220 of the base trial 182, and a knob 256 secured to the neck 254. The knob 256 is contoured such that a surgeon may grip the knob 256 rotate the fastener 242 relative to the base trial 182 (see FIG. 8). The button head 244 also has a socket 258 defined therein, which is sized to receive a driver or other surgical tool to rotate the fastener 242.

Figure 9:
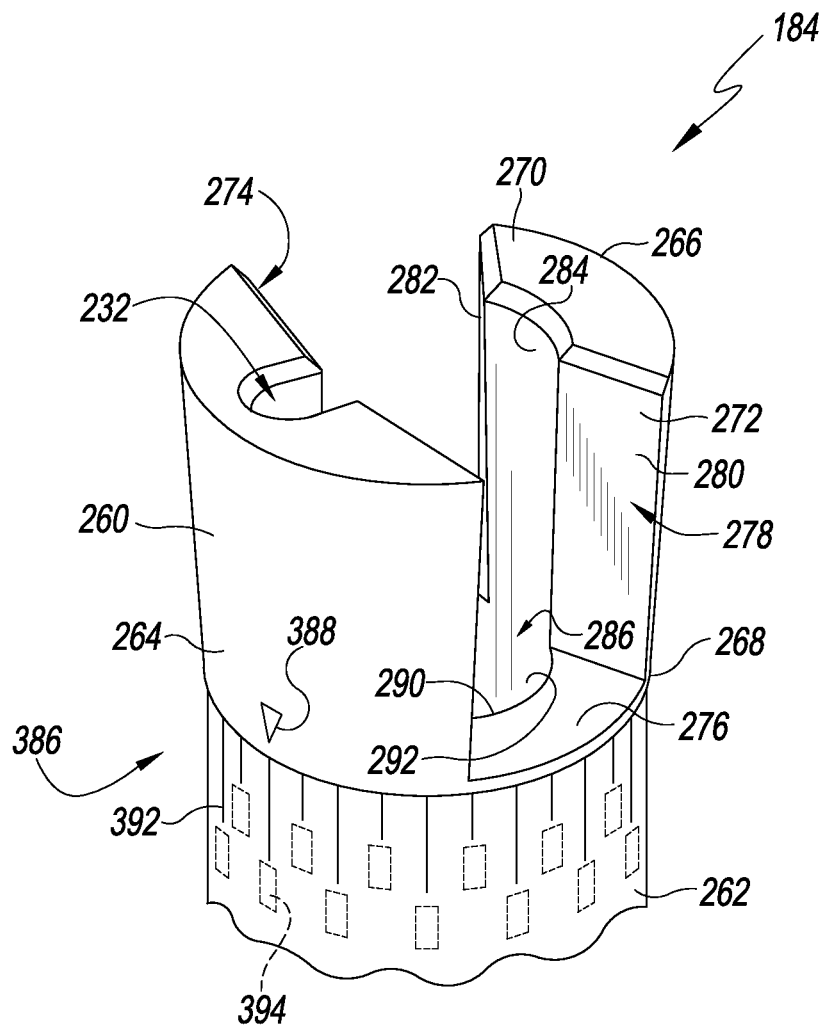
FIG. 9 is a fragmentary perspective view of an offset stem adaptor of the tibial trial assembly of FIG. 6.
Figure 10:
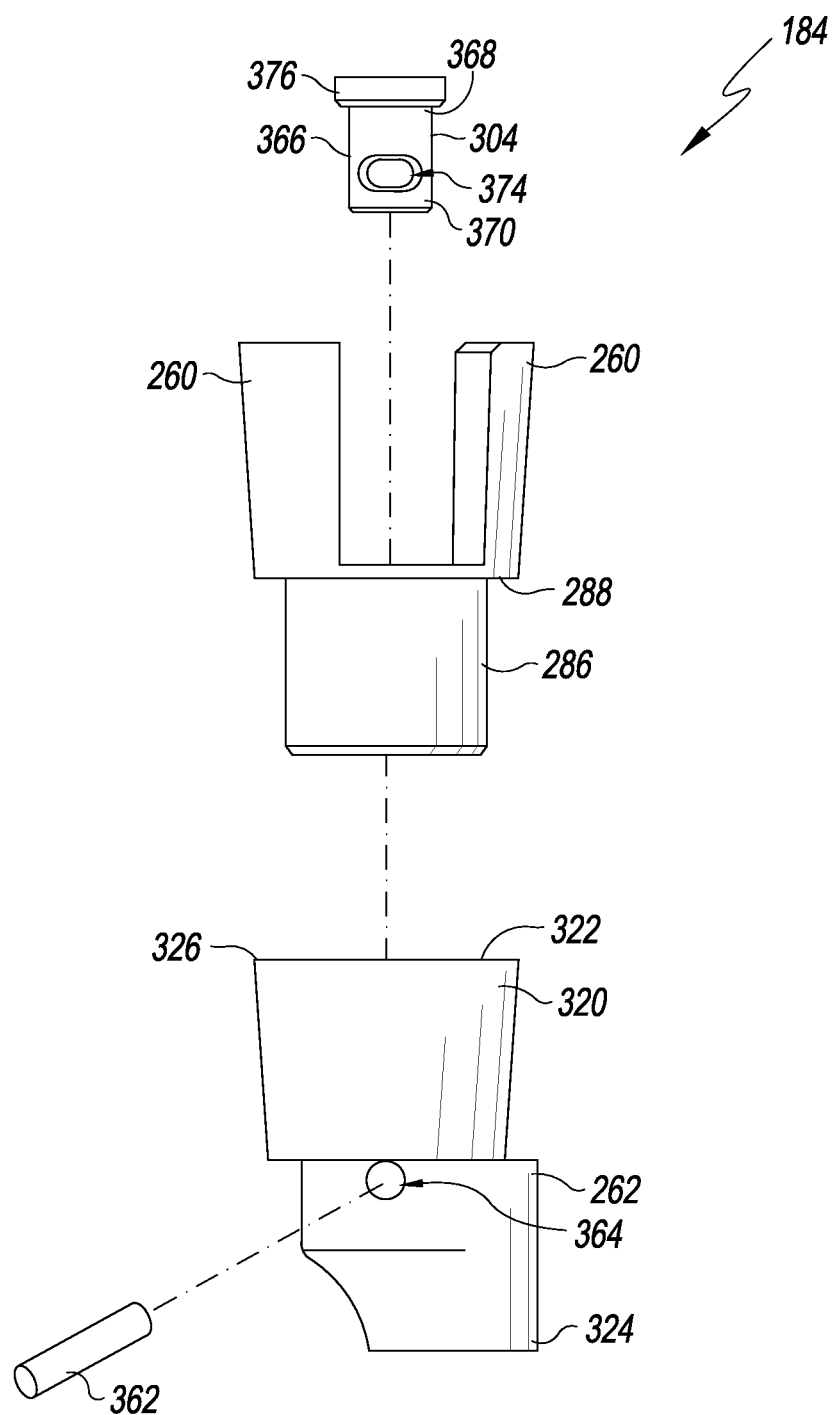
FIG. 10 is an exploded side elevation view of the offset stem adaptor of FIG. 9.

Referring now to FIGS. 9-12, the offset stem adaptor 184 of the tibial base trial assembly 180 includes an upper body 260 pivotally coupled to a lower body 262. It should be appreciated that other offset stem adaptors having different configurations may be provided. For example, bodies 260, 262 may have outer diameters and/or lengths that vary to fit different sized canals to accommodate prosthetic components of different sizes. As shown in FIG. 10, the upper body 260 includes a shell 264 extending from upper end 266 to a lower end 268. In the illustrative embodiment, the outer surface of the shell 264 is tapered, with the diameter of the upper body 260 decreasing between the ends 266, 268.

The shell 264 includes a substantially planar top surface 270 at the upper end 266 thereof. As shown in FIG. 9, the upper body 260 has inner walls 272, 274 that extend downwardly from the top surface 270. The walls 272, 274 cooperate with a base wall 276 to define a slot 278 extending through the top surface 270 and the outer surface of the shell 264. In the illustrative embodiment, the inner wall 272 has a planar surface 280 that extends at an oblique angle relative to another planar surface 282. An arcuate surface 284 connects the surfaces 280, 282. The arcuate surface 284 of the inner wall 272 is sized and shaped to engage the outer sleeve 250 of the fastener 242 configured to secure the base trial 182 to the stem adaptor 184.

The other inner wall 274 has a notch 232 defined therein. The notch 232 extends downwardly from the top surface 270 of the upper body 260 and opens into the slot 278. As described above, the notch 232 receives the pin 230 extending downwardly from the lower surface 194 of the trial plate 190 when the base trial 182 is secured to the stem adaptor 184. In the illustrative embodiment, the notch 232 is sized to prevent relative axial movement between the base trial 182 and the stem adaptor 184.

As shown in FIG. 10, the upper body 260 of the adaptor 184 has a plug 286 that is sized to be received in the lower body 262. The plug 286 extends downwardly from the shell 264, and, in the illustrative embodiment, is substantially cylindrical. The plug 286 cooperates with the shell 264 to define an annular flange 288 of the upper body 260. As described in greater detail below, the annular flange 288 is configured to engage the lower body 262 to prevent rotation between the bodies 260, 262.

Figure 11:
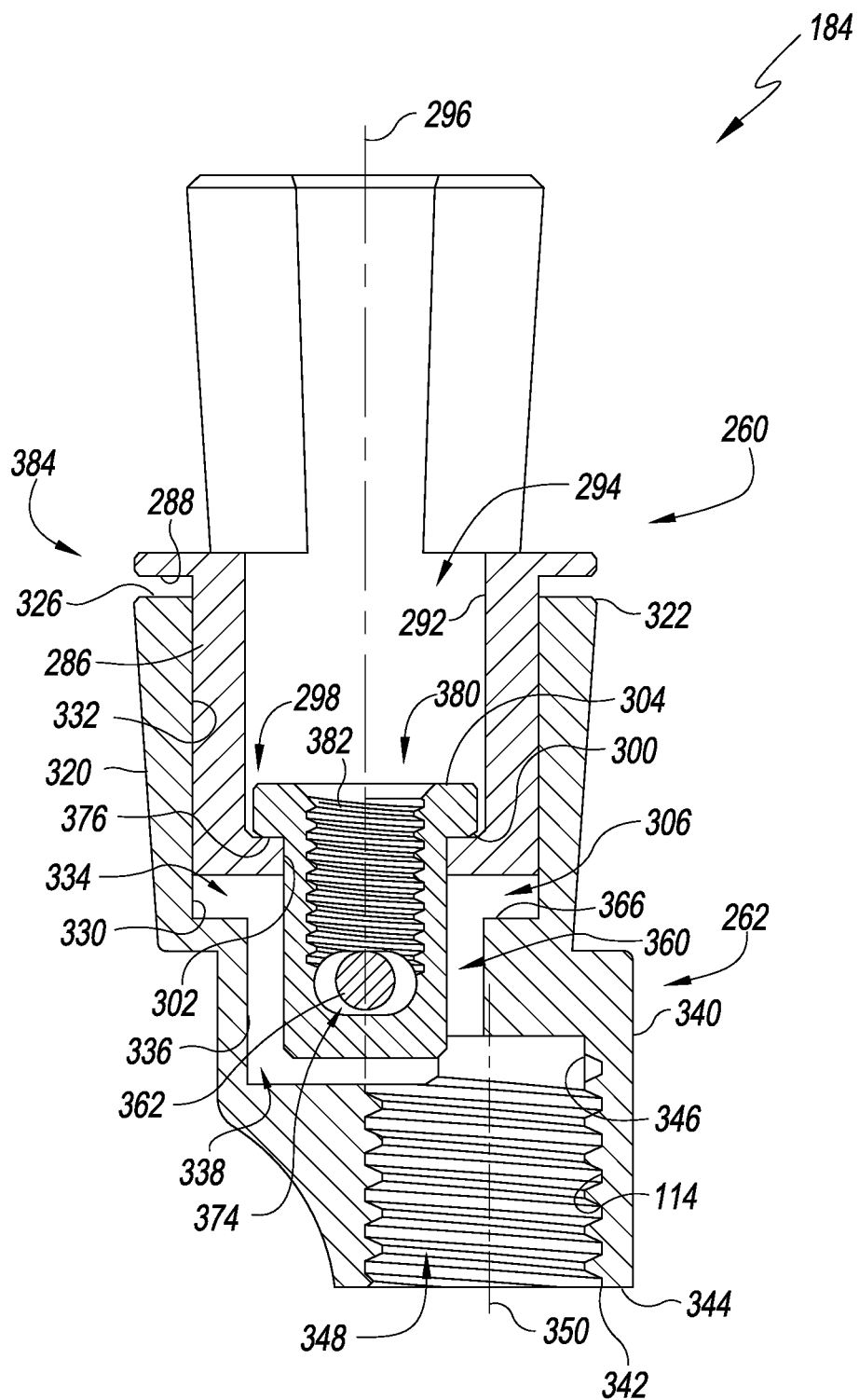
FIG. 11 is a cross sectional elevation view of the offset stem adaptor of FIG. 9 in an unlocked position.

Returning to FIG. 9, the base wall 276 of the upper body 260 has an opening 290 defined therein and an inner wall 292 that extends downwardly from the opening 290. The inner wall 292 defines a cylindrical passageway 294 in the plug 286. The passageway 294 is sized to receive the outer sleeve 250 of the fastener 242. As shown in FIG. 11, a longitudinal axis 296 extends through a lower end 298 of the passageway 294 and the opening 290.

A bottom wall 300 of the upper body 260 extends inwardly from the inner wall 292 to define the lower end 298 of the passageway 294. The bottom wall 300 has a central opening 302 defined therein, which extends through the entire thickness of the bottom wall 300. The central opening 302 is sized to receive a lug or insert 304 of the fastener 306 that couples the upper body 260 to the lower body 262, as described in greater detail below.

As described above, the stem adaptor 184 includes a lower body 262 that is pivotally coupled to the upper body 260. As shown in FIG. 10, the lower body 262 includes a plug housing 320 extending from upper end 322 to a lower end 324. In the illustrative embodiment, the outer surface of the plug housing 320 is tapered, with the diameter of the lower body 262 decreasing between the ends 322, 324.

The plug housing 320 includes a substantially planar top surface 326 at the upper end 322 thereof. As shown in FIG. 11, an opening 328 is defined in the top surface 326, and an inner wall 330 extends downwardly from the top surface 326. The inner wall 330 includes an upper section 332 that defines a passageway 334 in the plug housing 320. In the illustrative embodiment, the passageway 334 is sized to receive the plug 286 of the upper body 260. The inner wall 330 also includes a lower section 336 that defines an aperture 338 positioned below the passageway 334.

The lower body 262 also includes a shaft 340 that extends downwardly from the plug housing 320 and is configured to be secured to the stem trial 14. As shown in FIG. 11, the shaft 340 has an opening 342 defined in the end surface 344 thereof, and an inner wall 346 extends upwardly from the opening 342. The inner wall 346 and the opening 342 cooperate to define an aperture 348. In the illustrative embodiment, the inner wall 346 of the lower body 262 has a plurality of internal threads 114 formed thereon, which are configured to engage the external threads 116 of the stem trial 14 to secure the stem trial 14 to the offset stem adaptor 184.

In the illustrative embodiment, the aperture 348 is connected to the aperture 338. The aperture 348 defines an axis 350 that is offset from and extends parallel to the axis 296 of the upper body 260. When the stem trial 14 is attached to the stem adaptor 184, the longitudinal axis 136 is coincident with the axis 350.

Figure 12:
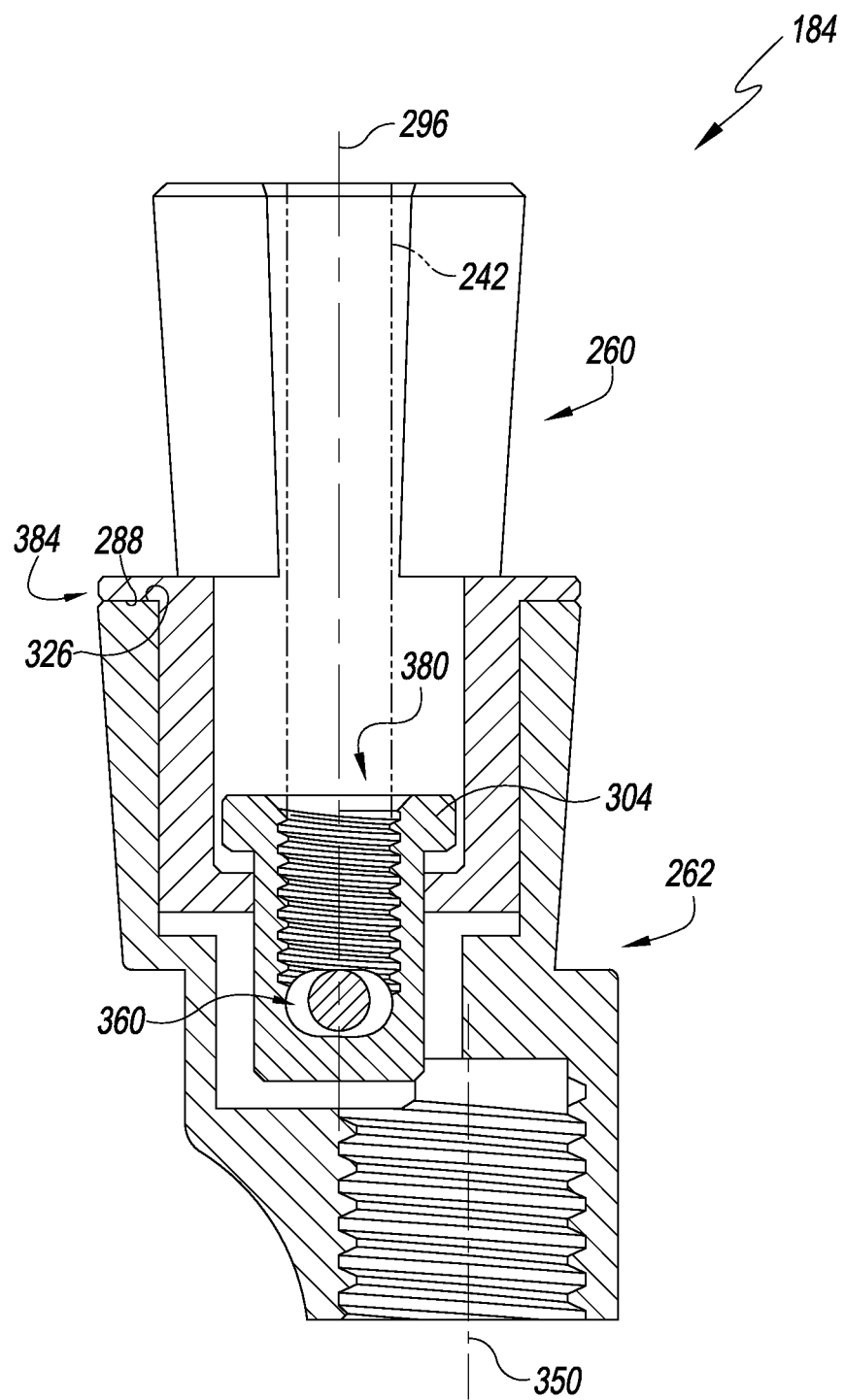
FIG. 12 is a view similar to FIG. 11 of the stem adaptor in a locked position.

As shown in FIGS. 10-12, the lower body 262 is coupled to the upper body 260 via a fastener 306. The fastener 306 includes an insert 304 that extends through the upper body 260 and is secured to the lower body 262 via a joint 360. The joint 360 includes a cylindrical pin 362 extending through a pair of bores 364 defined in the lower body 262. The pin 362 is sized to press fit into the bores 364. It should be appreciated that in other embodiments the pin 362 may be welded, threaded, or secured to the lower body 262 by other fastening means.

As shown in FIG. 10, the insert 304 has a cylindrical body 366 that extends from an upper end 368 to a lower end 370. The pin 362 of the joint 360 extends through an oblong slot 374 defined in the lower end 370 of the insert 304. In that way, the pin 362 secures the insert 304 to the lower body 262. As shown in FIG. 11, the body 366 of the insert 304 is sized to extend through the central opening 302 of the upper body 260.

The insert 304 also includes an annular flange 376 extending outwardly from the upper end 368 of the body 366. The flange 376 is larger than the opening 302 defined in the upper body 260 such that it engages bottom wall 300 of the upper body 260. In that way, the insert 304 is prevented from passing fully through the opening 302. The upper body 260 is also thereby secured to the lower body 262.

The insert 304 also includes a socket 380 configured to engage the fastener 242 to secure the offset adaptor 184 to the base trial 182. In the illustrative embodiment, the socket 380 is defined in the upper end 368 of the body 366. A plurality of internal threads 382 are defined in the wall defining the socket 380. The threads 382 are configured to engage the external threads 252 of the fastener 242 to secure the offset adaptor 184 to the base trial 182.

As described above, the lower body 262 is pivotally coupled to the upper body 260. As a result, when the upper body 260 is prevented from rotating, the lower body 262 may be pivoted about the axis 296 of the upper body 260. Conversely, when the lower body 262 is prevented from rotating, the upper body 260 may be pivoted about the axis 350 of the lower body 262. The offset adaptor 184 also includes a locking mechanism 384 configured to lock the upper body 260 and the lower body 262 in position relative to each other. In the illustrative embodiment, the locking mechanism 384 includes the insert 304.

As shown in FIGS. 11 and 12, the insert 304 may be moved along the axis 296 of the upper body 260 between an unlocked position and a locked position. In the unlocked position shown in FIG. 11, the top surface 326 of the plug housing 320 is spaced apart from the annular flange 288 of the upper body 260. When the fastener 242 is threaded into the insert 304, the insert 304 may be advanced upward along the axis 296. The engagement between the insert 304 and the joint 360 causes the lower body 262 to be drawn upward with the insert 304. When the insert 304 is advanced to the locked position shown in FIG. 12, the top surface 326 of the plug housing 320 engages the annular flange 288 of the upper body 260, thereby preventing movement between the lower body 262 and the upper body 260.

Returning to FIG. 9, the tibial base trial assembly 180 includes an offset indicator 386 configured to indicate the offset orientation between the stem trial 14 and the tibial base trial 182. In the illustrative embodiment, the offset indicator 386 includes a marking 388 defined on the upper body 260 of the stem adaptor 184 and a plurality of markings 390 defined on the lower body 262. Each marking 390 corresponds to one of the markings 142 on the offset tool 76 and hence to a different offset orientation of the revision tibial prosthesis 600. In the illustrative embodiment, the marking 388 is arrow-shaped, and the markings 390 include lines 392 and numerical indicators 394 associated with the lines 392 to identify the offset orientations. When the marking 388 is aligned with one of the lines 392, the numerical indicator 394 corresponding to that line 392 may be read to determine the offset orientation.

Returning to FIG. 6, the tibial tray trial assembly 180 also includes a base insert 186 configured to be positioned in the plate opening 198 of the base trial 182. The base insert 186 has a lower surface 400 configured to engage the shelf surface 218 of the base trial 182 when the base insert 186 is seated on the base trial 182. The base insert 186 also includes a central frame 402 sized to be received in the central opening 200 of the base trial 182. The central frame 402 has a cylindrical slot 404 defined therein, which is sized to receive the platform 220 of the base trial 182. A lug 406 extends upwardly from the central frame 402 adjacent to the slot 404.

The base insert 186 also includes a pair of prongs 410, 412 that extend outwardly from the central frame 402. The prongs 410, 412 are sized to be received in the elongated openings 202 of the base trial 182. Each of the prongs 410, 412 has a bore 414 defined therein. The bores 414 are sized to receive pegs 416 of an attachment tool 418, as described in greater detail below.

In the illustrative embodiment, the base insert 186 also includes a keel punch 420 shaped to form an opening in the patient's tibia sized to receive the keels 630 of a prosthetic tibial tray 602. The keel punch 420 includes a pair of lower arms 422 that extend downwardly from the prongs 410, 412. Each lower arm 422 has a plurality of cutting teeth 426 formed thereon. As described in greater detail below, the system 10 may also include a check base insert 428 (see FIG. 13) that does not include a keel punch 420.

As described above, the instrument system 10 also includes an attachment tool 418 configured to position the base insert 186 in the base trial 182. In the illustrative embodiment, the attachment tool 418 includes a main body 430 and a pair of arms 432, 434 extending outwardly from the main body 430. A peg 416 extends downwardly from each of the arms 432, 434. Each peg 416 is sized to be positioned in a corresponding bore 414 of the base insert 186. Each peg 416 has an annular slot 436 defined therein, and a biasing element 438 is positioned in the slot 436. The biasing element 438 is configured to engage the walls of the bore 414 when the peg 416 is positioned therein to secure the base insert 186 to the attachment tool 418. In the illustrative embodiment, the biasing element 438 is a ring-shaped coil. It should be appreciated that in other embodiments the spring may take the form of another biasing or friction element, such as, for example, an o-ring or a retaining ring.

The attachment tool 418 has an opening (not shown) that is sized to receive the button head 244 of the fastener 242 when the attachment tool 418 is used to position the base insert 186 on the base trial 182. As shown in FIG. 6, the attachment tool 418 also includes a socket 444 configured to receive a catch 732 and a mounting rod (not shown) of a system handle 730 (see FIG. 28).

As described above, the system 10 also includes a number of tibial bearing trial assemblies 450. An exemplary tibial bearing trial assembly 450 is disclosed in U.S. patent application Ser. No. 13/530,649, filed Jun. 22, 2012 and entitled "TRIALING SYSTEM FOR A KNEE PROSTHESIS AND METHOD OF USE," by Thomas E. Wogoman et al., which is incorporated herein by reference. It should be appreciated that in other embodiments the tibial bearing trial may be a monolithic component, and the system 10 may include multiple tibial bearing trials different sizes and configurations.

Figure 13:
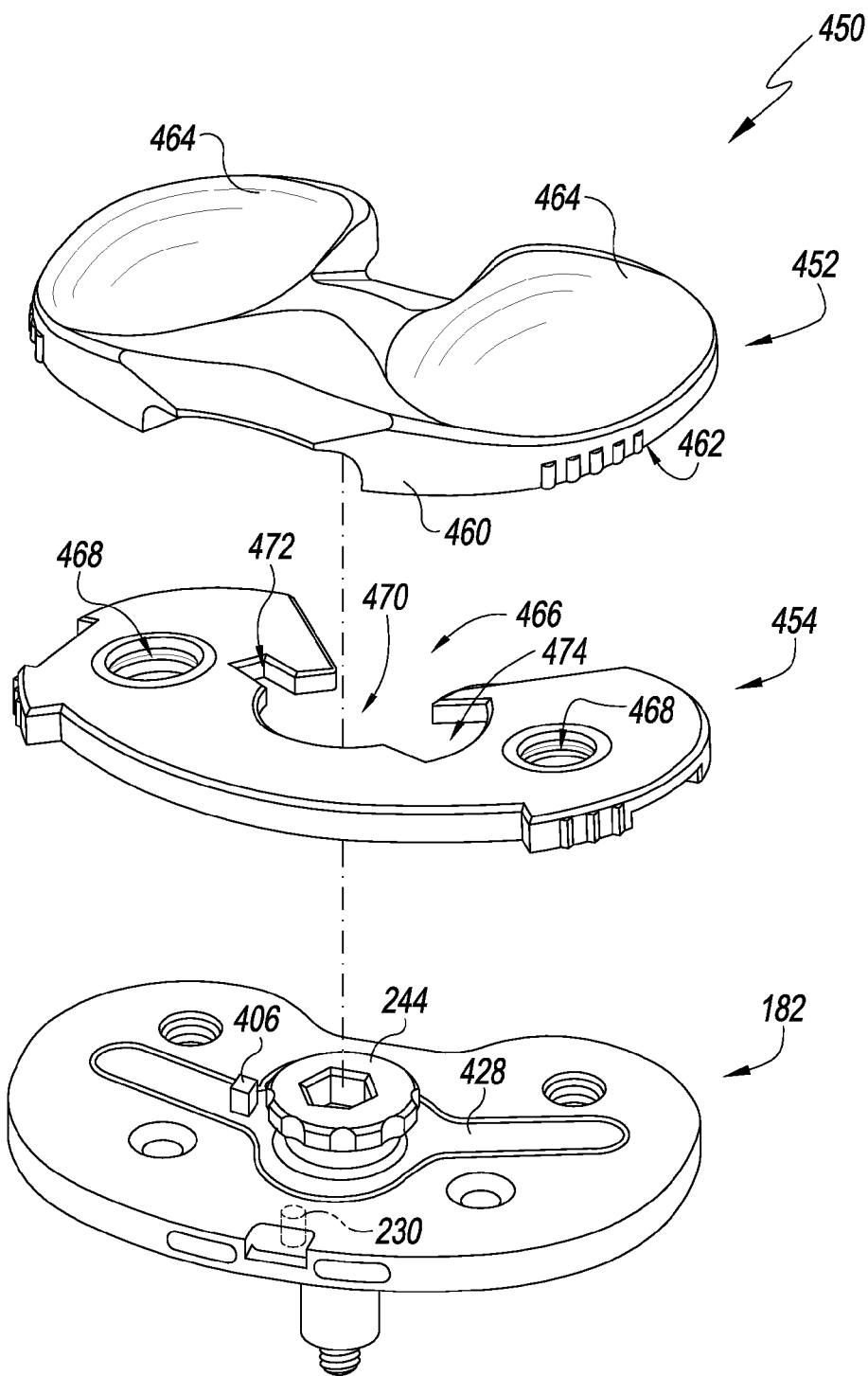
FIG. 13 is an exploded perspective view of the tibial base trial of FIG. 7 and a tibial bearing trial.

Referring now to FIG. 13, each tibial bearing trial assembly 450 is a multi-piece assembly configured to assist the surgeon in selecting a size and configuration of a prosthetic tibial bearing component of the knee prosthesis. A tibial bearing trial 450 may be assembled with one of a number of tibial bearing surface trials 452 and one of a number of a plurality of trial shims 454. Each bearing surface trial 452 has a different size and/or configuration, and each shim 454 has a different thickness. Because each shim 454 is configured to be secured to each bearing surface trial 452, the surgeon is able to assemble a tibial bearing trial 450 of one size and configuration, evaluate the performance of that tibial bearing trial 450, and then modify the tibial bearing trial 450 as necessary to determine intraoperatively the type and configuration of the prosthetic tibial bearing component to be implanted.

In the illustrative embodiment, each of the bearing surface trials 452 is a fixed bearing surface trial. The term "fixed bearing surface trial" as used herein refers to a bearing surface trial that is fixed in position relative to the tibial base trial 182 when the bearing surface trial and shim are attached thereto (i.e., it is configured to not substantially rotate or move in the anterior-posterior direction or medial-lateral direction relative to the tibial base trial 182). The fixed bearing surface trial 452 may be embodied as a cruciate retaining trial, a posterior stabilized trial, a revision trial, or other surface trial configuration, per the surgeon's preference. For example, in embodiments where the fixed bearing surface trial 452 is embodied as a posterior stabilized trial, the fixed bearing surface trial 452 may include a spine extending upwardly from the upper bearing surface of the trial 458.

The fixed bearing surface trial 452 has a platform 460 including a lower surface 462 that contacts the shim 454 when the shim 454 is secured thereto. The platform 460 also includes a pair of articulation surfaces 464 that are positioned opposite the lower surface 462. The articulation surfaces 464 are configured to articulate with the condyle surfaces of a femoral surgical instrument of a femoral prosthetic component.

As described above, each of the surface trials 452 are configured to be secured with a trial shim 454. The shim 454 has an aperture 466 defined therein, which is configured to receive the button head 244 of the fastener 242 and the lug 406 of the base insert 186 when the shim 454 is positioned on the base trial 182. Each shim 454 also includes a pair of through-holes 468, which are configured to receive fastener pegs (not shown) of the tibial bearing surface trials 452 to secure the shim 454 to each trial 452.

The aperture 466 also includes a central passageway 470, a rectangular slot 472 extending outwardly from the central passageway 470, and an arcuate slot 474. The central passageway 470 is sized to receive the button head 244. The rectangular slot 472 is sized to receive the lug 406 when the shim 454 is attached to a fixed bearing surface trial 452 on the base trial 186.

Referring now to FIGS. 14-18, the instrument system 10 includes a removal tool 500 configured to engage the tibial base trial assembly 180 to remove the tibial base trial assembly 180 from the proximal end of the patient's tibia. The removal tool 500 has a housing 502 that extends from an upper end 504 to a lower end 506. The housing 502 includes a socket 508 defined in the upper end 504 that is configured to engage a catch 732 and a mounting rod (not shown) of a system handle 730 (see FIG. 28), and a socket 510 defined in the lower end 506 that is configured to engage the tibial base trial assembly 180.

As shown in FIG. 15, the socket 508 includes a central aperture 512 defined in an upper surface 514 of the housing 502. The socket 508 also includes an outer slot 516 defined in a side wall 518 of the housing 502 and the upper surface 514. The slot 516 is defined by an inner wall 520 extending inwardly from the side wall 518 and another inner wall 522 extending upwardly from the inner wall 520. A flange 524 extends from the inner wall 522 to define a notch 526 that receives a catch 732 of the system handle 730, as described in greater detail below.

The socket 510 of the removal tool 500 includes a slot 530 that extends inwardly from the side wall 518. In the illustrative embodiment, the slot 530 is sized to receive the knob 256 of the fastener 242. The socket 510 also includes a pair of engagement arms 532 that define an opening 534 sized to receive the neck 254 of the button head 244. In that way, each arm 532 is configured to be positioned between the knob 256 of the fastener 242 and the plate 190 of the tibial base trial 182.

Figure 18:
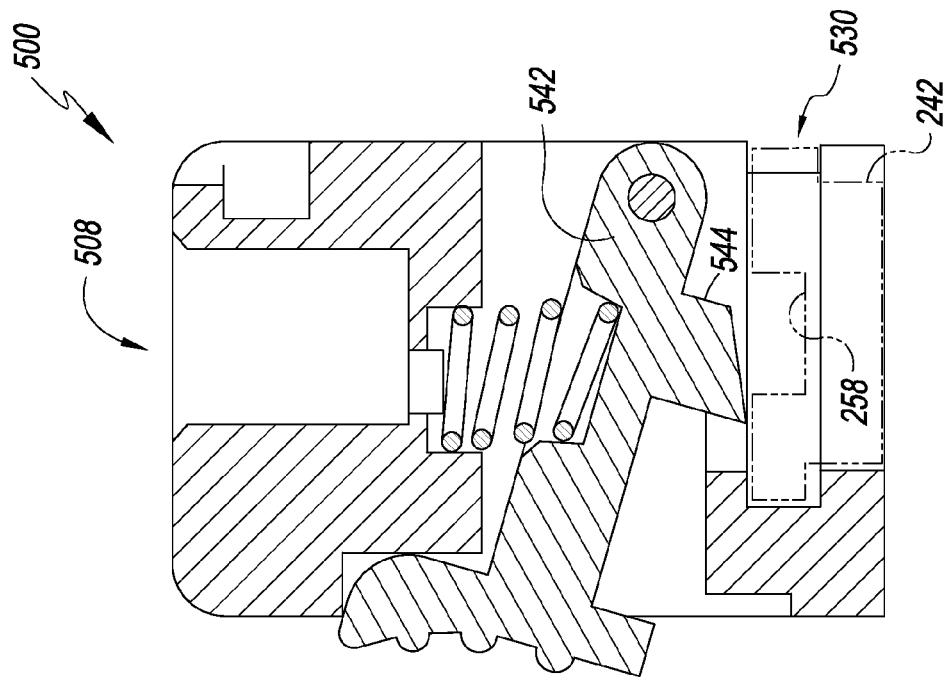
FIG. 18 is a view similar to FIG. 17 showing the locking mechanism in an unlocked position.
Figure 17:
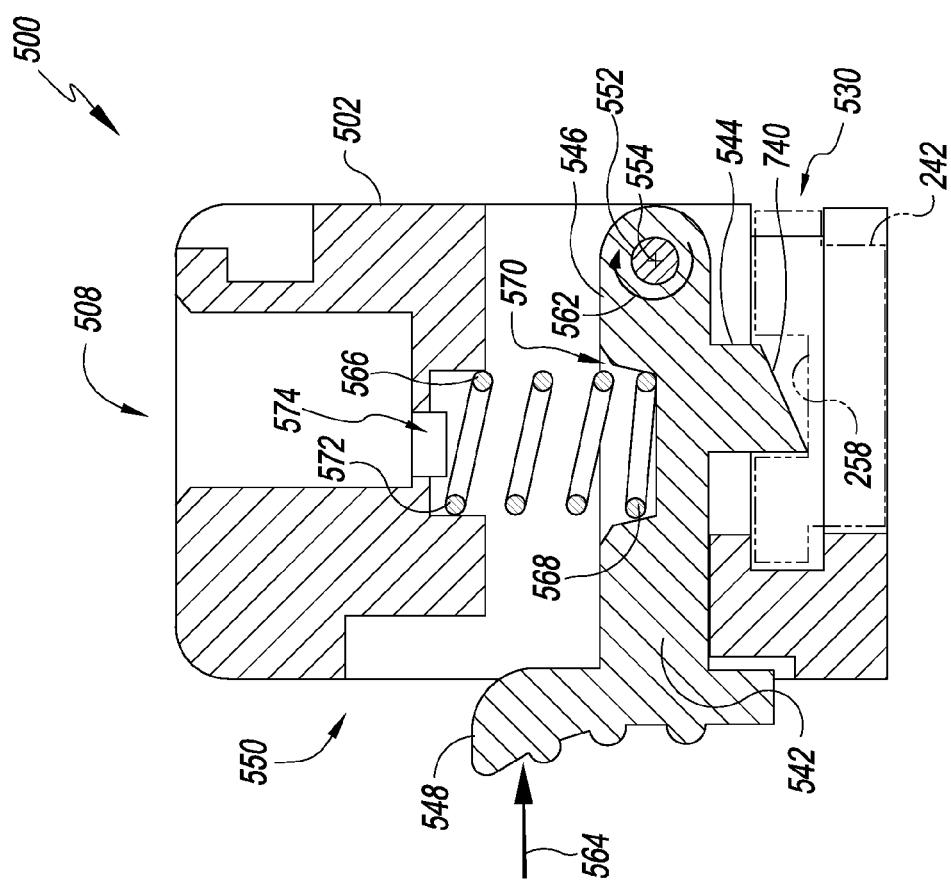
FIG. 17 is a cross sectional elevation view of the removal tool of FIGS. 14-16 showing a locking mechanism in a locked position.

As shown in FIG. 14, the removal tool 500 further includes a locking mechanism 540 configured to secure the tibial base trial 182 to the removal tool 500. In the illustrative embodiment, the locking mechanism 540 includes a lever 542 and a dowel pin 544 attached to the lever 542. The lever 542 is pivotally coupled to the housing 502. As shown in FIG. 17-18, the dowel pin 544 may be moved into and out of engagement with the socket 258 defined in the fastener 242 of the base trial assembly 180.

The lever 542 of the removal tool 500 includes a support arm 546 positioned above the slot 530 and an actuation arm 548 positioned in an opening 550 defined in the housing 502. As shown in FIG. 17, the dowel pin 544 extends downwardly from the support arm 546. The support arm 546 has pair of pins 552 that define a pivot axis 554 of the lever 542. Each pin 552 is received in a corresponding hole 556 defined in the housing 502 to attach the lever 542.

As shown in FIG. 16, the actuation arm 548 of the lever 542 includes a contoured surface 560, which may be pressed by the user to pivot the lever 542 about the axis 554. In the illustrative embodiment, when force is applied to the actuation arm 548 in the direction indicated by arrow 564, the lever 542 is rotated in the direction indicated by arrow 562. When the lever 542 is rotated about the axis 554 as indicated by arrow 562, the lever 542 is moved between a locked position (see FIG. 17) in which the dowel pin 544 is positioned in the socket 258 and an unlocked position (see FIG. 18) in which the dowel pin 544 is spaced apart from the socket 258 when the removal tool 500 is positioned over the base trial 182.

The locking mechanism 540 includes a biasing element 566 that resists movement of the lever 542 in the direction indicated by arrow 562. In the illustrative embodiment, the biasing element 566 is a spring 566 that has a lower end 568 positioned in a groove 570 defined in the support arm 546. The spring 566 has an upper end 572 positioned in a recess 574 defined in the housing 502. As shown in FIGS. 17-18, the spring 566 biases the lever 542 in the locked position.

Figures 19, 19A:
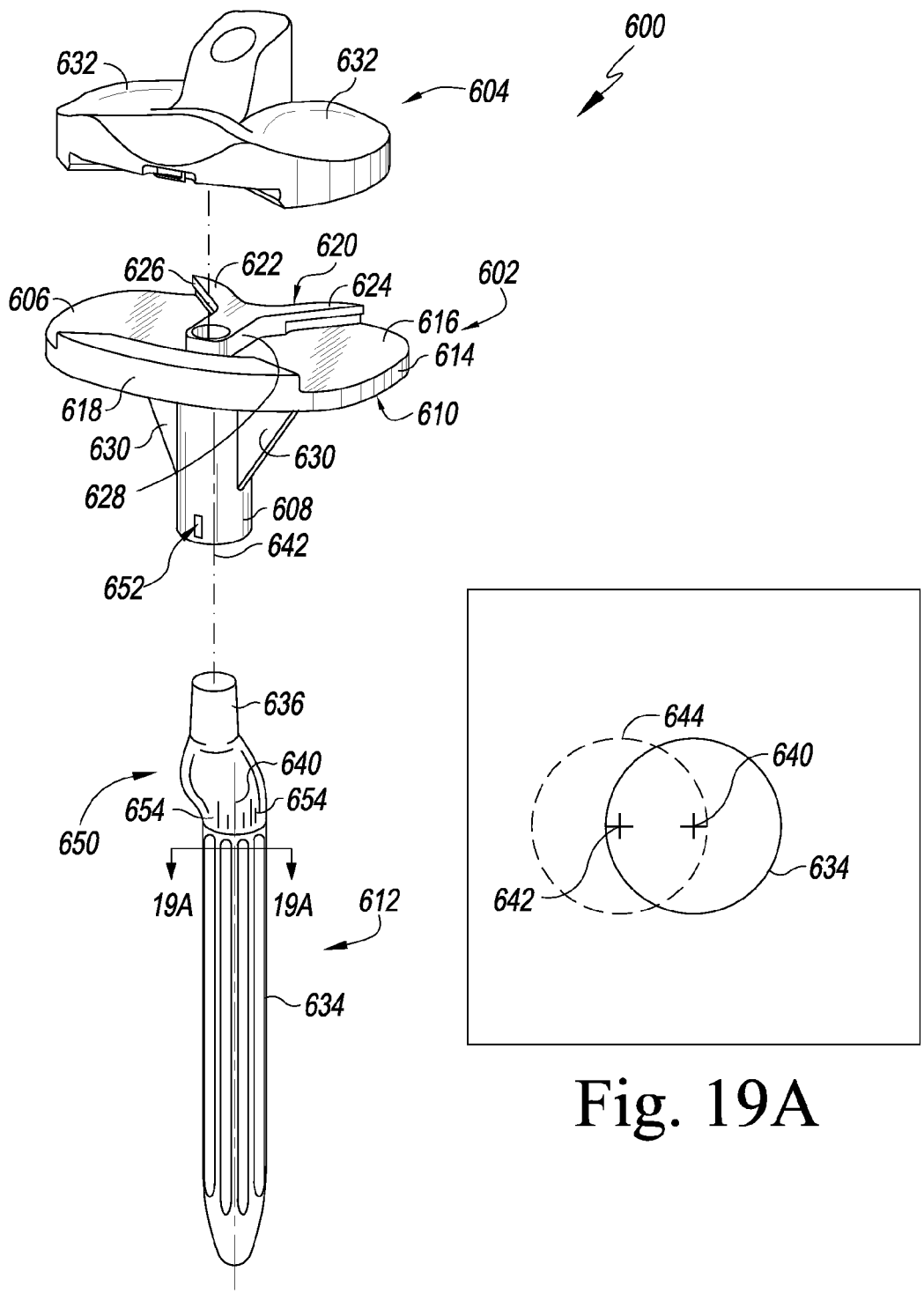
FIG. 19 is an exploded perspective view of a revision prosthetic tibial component.
FIG. 19A is a diagrammatic view of the revision prosthetic tibial component of FIG. 19 taken along the line 19A-19A in FIG. 19.
Figure 20:
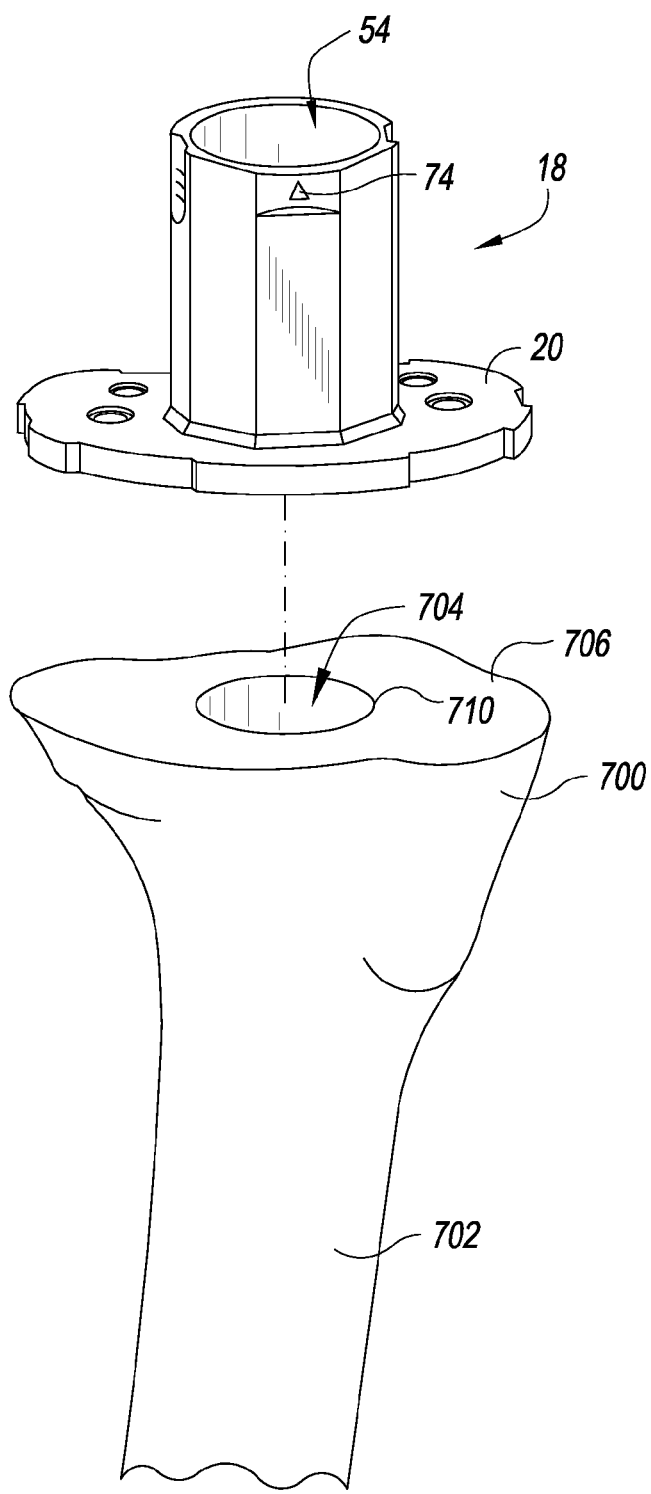
FIGS. 20-29 show the instruments of the orthopaedic surgical instrument system being used to surgically prepare a proximal end of a patient's tibia to receive the revision prosthetic tibial component of FIG. 19.

The instrument system 10 described above may be utilized during the performance of an orthopaedic surgical procedure to implant a revision tibial prosthesis 600. One embodiment of the revision tibial prosthesis 600 is shown in FIGS. 19-20. The prosthesis 600 includes a prosthetic tibial tray 602 and a bearing 604 securable to the tray 602. The tray 602 includes a platform 606 having a fixation member, such as a stem post 608, extending away from its lower surface 610. The prosthesis 600 also includes a stem component 612 that is securable to the stem post 608 of the tray 602. The stem post 608 and component 612 are configured to be implanted into the proximal end of the patient's tibia.

The platform 606 is shaped to be positioned on the surgically-prepared proximal end of the patient's tibia. As shown in FIG. 19, the platform 606 has an outer wall 614 that extends between the lower surface 610 and an upper surface 616. The outer wall 614 defines the outer profile of the platform 606 and includes a convex anterior section 618 and a concave posterior section 620. It should be appreciated that the tibial trays of different sizes may be manufactured to fit bones of varying size. In such embodiments, the platform 606 may be larger or smaller to better conform to the bony anatomy of the patient.

The platform 606 also includes a generally Y-shaped posterior buttress 622 that extends upwardly from an upper surface 616. The posterior buttress 622 includes a pair of arms 624, 626 extending along a posterior section of the perimeter of the platform 606. A third arm 628 extends anteriorly away from the intersection of the lateral arm 624 and the medial arm 626 (i.e., in a direction toward the center of the platform).

A pair of keels 630 extends downwardly from the lower surface 610 of the platform 606. Each keel 630 extends outwardly from the stem post 608 of the tray 602.

As described above, the bearing 604 of the prosthesis 600 is securable to the tibial tray 602. In particular, the bearing 604 may be snap-fit to the tibial tray 602. In such a way, the bearing 604 is fixed relative to the tibial tray 602 (i.e., it is not rotatable or moveable in the anterior-posterior or medial-lateral directions). The bearing 604 also includes a pair of concave bearing surfaces 632 shaped to engage the condyle surfaces of a prosthetic femoral component or the patient's natural condyles.

As described above, the prosthesis 600 also includes a stem component 612 that is securable to the stem post 608 of the tray 602. As shown in FIG. 19, the component 612 includes an elongated body 634 that extends downwardly from a head 636. The head 636 is shaped to be received in an aperture 638 defined in the stem post 608 of the tray 602. The prosthesis 600 includes a fastener (not shown) to secure the stem component 612 to the tray 602. The fastener may include a taper fit between the head 636 and the aperture 638, a threaded fastener, or other fastening device.

As shown in FIG. 19, the elongated body 634 of the stem component 612 has a longitudinal axis 640 that is offset from and extends parallel to a longitudinal axis 642 of the tray stem post 608. In the illustrative embodiment, the axis 640 is offset from the axis 642 by approximately four millimeters. As shown in FIG. 19A, the stem component 612 may be rotated relative to the tibial tray 602 such that the axis 640 defines a circular path 644 about the axis 642. In that way, the elongated body 634 of the stem component 612 may be offset from the stem post 608 in any orientation about the axis 642.

The prosthesis 600 also includes an offset indicator 650 configured to indicate the offset orientation between the stem component 612 and the tibial tray 602. In the illustrative embodiment, the offset indicator 650 includes a marking 652 defined on the tray stem post 608 and a plurality of markings 654 defined on the body 634 of the component 612. Each marking 654 corresponds to a different offset orientation. In the illustrative embodiment, each marking 654 further corresponds to one of the markings 142 defined on the offset tool 76 of the guide assembly 12 and to one of the markings 390 defined on the stem adaptor 184 of the trial base assembly 180. In the illustrative embodiment, the marking 652 is a raised elongated rib, and the markings 654 include lines 656 to identify the offset orientation of the stem component 612 when aligned with the marking 652.

Figure 22:
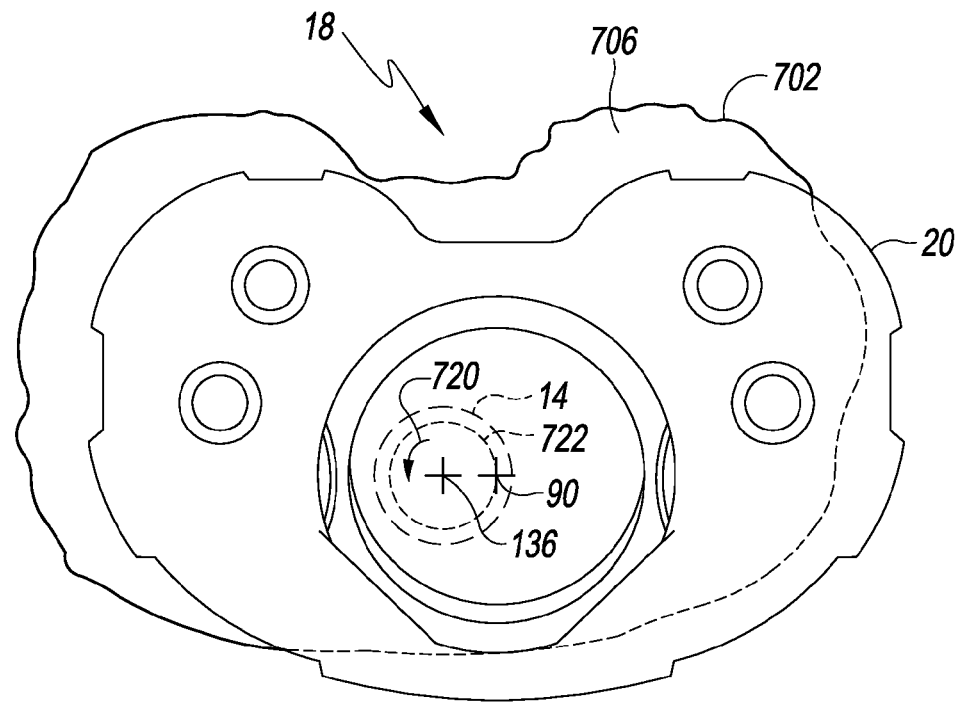
Figure 23:
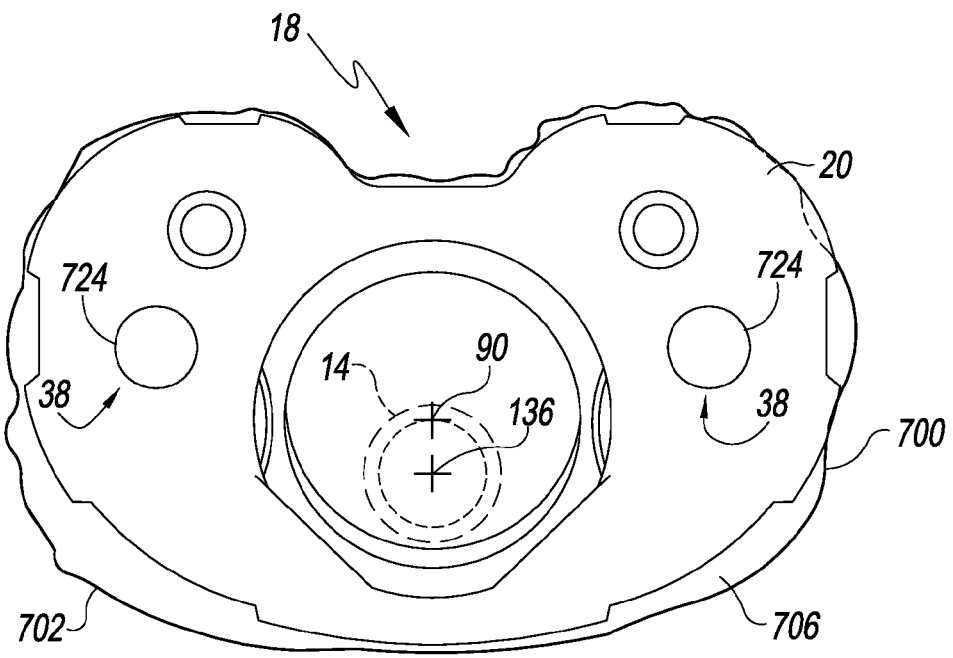
Figure 24:
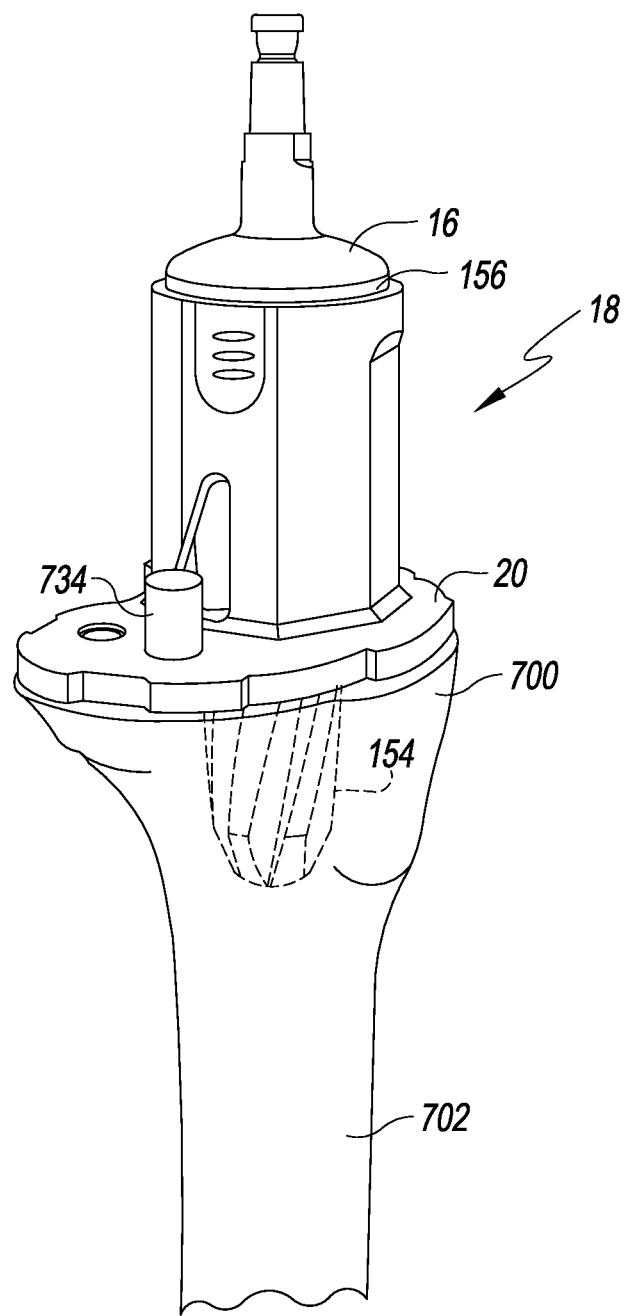

As described above, the instrument system 10 may be utilized during the performance of an orthopaedic surgical procedure to implant the revision tibial prosthesis 600 into a proximal end 700 of a patient's tibia 702, which are shown in FIG. 19A. To do so, the surgeon may initially prepare the medullary canal 704 and perform a resection of the proximal end 700 of a patient's tibia 702 to surgically-prepare the proximal surface 706 to receive the offset guide instrument assembly 12. An exemplary method of preparing a medullary canal and performing a resection is shown and described in U.S. patent application Ser. No. 13/485,444 entitled "METHOD OF SURGICALLY PREPARING A PATIENT'S TIBIA," which is expressly incorporated herein by reference. After obtaining the surgically-prepared proximal surface 706, the surgeon may use the offset guide instrument assembly 12 to identify an initial offset orientation for the prosthesis 600, as shown in FIGS. 20-23. As shown in FIG. 24, the surgeon may then utilize the guide tower 18 to ream the medullary canal 704 before removing the guide tower 18 from the patient's tibia 702.

As shown in FIGS. 25-29, the surgeon may assemble a tibial tray trial assembly 180 and perform a trial reduction with a tibial bearing trial 450. The surgeon may then impact a base insert 186 into the patient's tibia 702 before removing the tibial tray trial assembly 180 therefrom.

Referring now to FIG. 20, the guide tower 18 may be positioned on the surgically-prepared proximal surface 706 of the patient's tibia 702 after initial preparation of the medullary canal 704 and performance of a resection of the proximal end 700. To do so, the surgeon aligns the passageway 54 of the guide tower 18 with the proximal opening 710 of the medullary canal 704, as shown in FIG. 20. The surgeon may then advance the base plate 20 into contact with the surgically-prepared proximal surface 706.

The surgeon may select a stem trial 14 from a plurality of stem trials and secure the selected stem trial 14 to the shaft 82 of the offset guide tool 76. With the guide tower 18 positioned on the patient's tibia 702, the surgeon may advance the stem trial 14 into the passageway 54 of the guide tower 18. The surgeon may continue to move the offset guide tool 76 downward to position the barrel body 80 in the passageway 54. In doing so, the stem trial 14 is advanced downward into the proximal opening 710 of the medullary canal 704. When the annular flange 122 of the knob 120 engages the upper end 46 of the guide tower housing 40, the stem trial 14 is seated in the medullary canal 704, as shown in FIG. 21.

Figure 21:
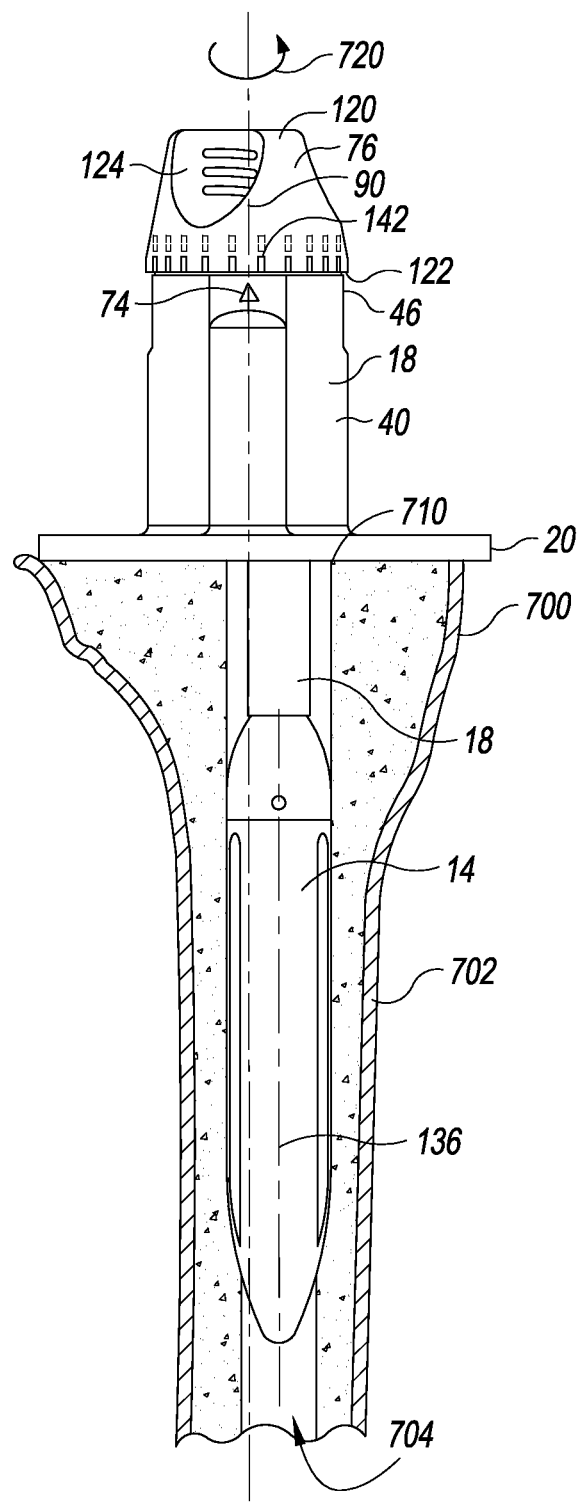

With the stem trial 14 seated in the medullary canal 704, the surgeon may grip the contoured outer surface 124 to turn the knob 120 about the axis 90 as indicated in FIG. 21 by arrow 720. As the knob 120 is turned, the offset guide tool 76 is rotated within the guide tower 18 about the axis 90 and the longitudinal axis 136 of the stem trial 14. Because the stem trial 14 is seated in the medullary canal 704, the stem trial 14 can only rotate about its longitudinal axis 136. As a result, the rotation of the tool 76 about its axis 90 causes the guide tower 18 to move along a circular path 722. When the offset guide instrument assembly is viewed in a transverse plane, as shown in FIGS. 22-23, the longitudinal axis 56 of the guide tower 18 is moved along the circular path 722 with the turning of the knob 120. That movement changes the position of the base plate 20 on the surgically-prepared proximal surface 706 of the patient's tibia 702 and changes the offset orientation of the guide tower 18 relative to the stem trial 14. The surgeon may continue to turn the knob 120 until the base plate 20 is placed in a location on the patient's tibia 702 that offers maximum coverage of the surgically-prepared proximal surface 706. When the base plate 20 is in the desired location on the patient's tibia 702, the surgeon examines the line 44 on the knob 120 aligned with the marking 74 on the guide tower 18 and reads the numerical indicator 146 to identify the selected offset orientation.

As shown in FIG. 24, the surgeon may then utilize the fastener holes 38 to advance bone pins 724 into patient's tibia 702, which secure the guide tower 18 in position on the surgically-prepared proximal surface 706. The offset guide tool 76 and the stem trial 14 may be removed from the guide tower 18, and the surgical reamer 16 aligned with the passageway 54. The surgeon may then advance the reamer 16 into the passageway to engage the cutting flutes 154 with the patient's tibia 702. The surgeon may continue to advance the reamer 16 deeper into the patient's tibia 702 until the indicator 156 is aligned with the upper end 46 of the housing 40, as shown in FIG. 24. The reamer 16 may then be removed from the guide tower 18, and the guide tower 18 removed from the patient's tibia 702.

Figure 25:
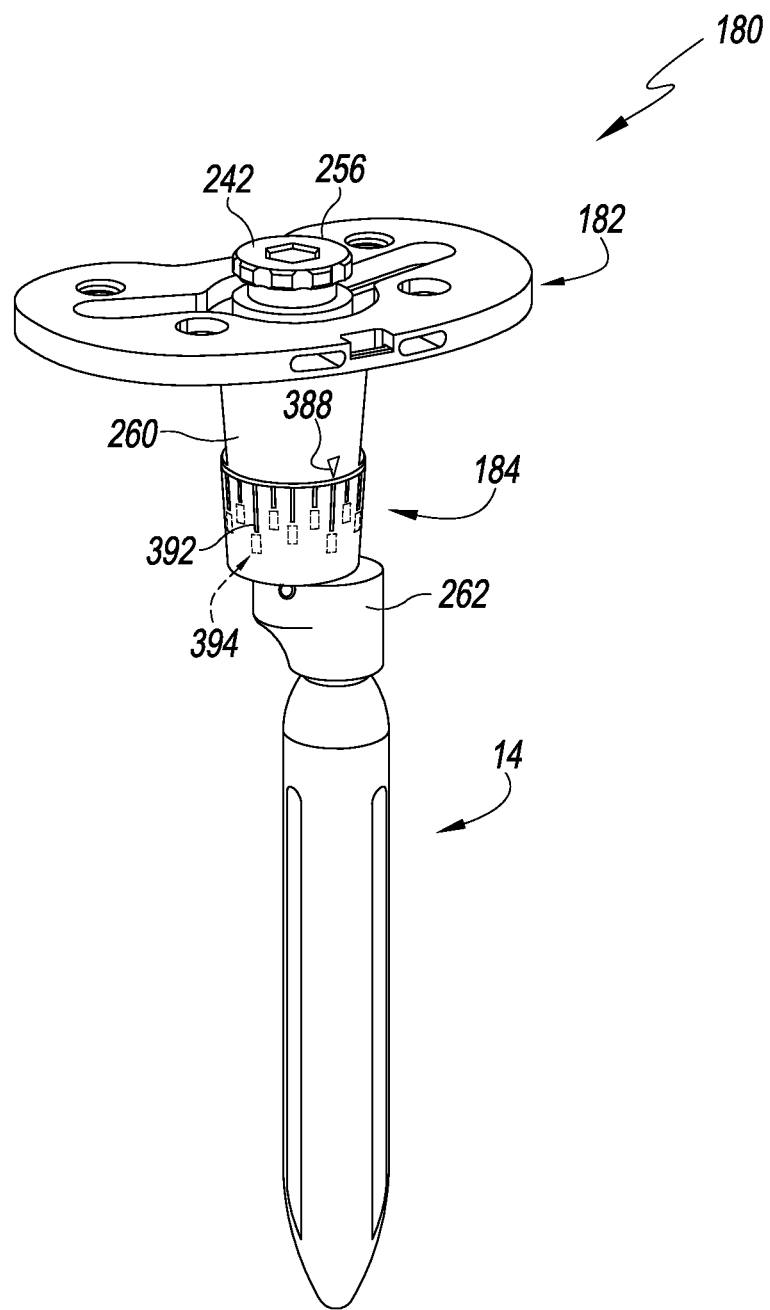

After performing the reaming operation, the surgeon may assemble a tibial tray trial 180. To do so, the surgeon may select a base trial 182 and an offset stem adaptor 184 and secure those instruments together with the stem trial 14, as shown in FIG. 25. To secure the stem trial 14 to the stem adaptor 184, the stem trial 14 is aligned with the aperture 348. The external threads 116 of the stem trial 14 may then be engaged with the internal threads 114 of the stem adaptor 184, thereby securing the stem trial 14 to the stem adaptor 184.

To secure the stem adaptor 184 to the base trial 182, the base trial 182 is aligned with the slot 278 of the stem adaptor 184. The central shaft 246 of the fastener 242 may be advanced through the slot 278 into the passageway 294 and into contact with the insert 304 of the stem adaptor 184. Concurrently, the pin 230 of the base trial 182 is advanced into the notch 232 defined in the stem adaptor 184. The external threads 252 formed on the fastener 242 may be engaged with the internal threads 382 of the insert 304. By turning the knob 256 of the fastener 242, the insert 304 may be threaded onto the central shaft 246.

Before fully seating the base trial 182 on the stem adaptor 184, the surgeon may rotate the lower body 262 relative to the upper body 260 to change the offset orientation of the stem trial 14. In doing so, the surgeon aligns the marking 388 defined on the upper body 260 with the line 392 and the numerical indicator 394 of the markings 392 corresponding to the offset orientation identified using the offset guide instrument assembly 12. In that way, the offset orientation identified prior to reaming the patient's tibia 702 is reproduced when trialing the tibial prosthetic components.

When the markings 388, 392 are properly aligned, the surgeon may turn the knob 256 of the fastener 242. As the knob 256 is turned, the insert 304 is advanced upward along the axis 296 of the stem adaptor 184. As described above, the engagement between the insert 304 and the joint 360 causes the lower body 262 to be drawn upward with the insert 304 until the top surface 326 of the plug housing 320 engages from the annular flange 288 of the upper body 260. The engagement between the flange 288 and the top surface 326 prevents movement between the lower body 262 and the upper body 260.

Figure 26:
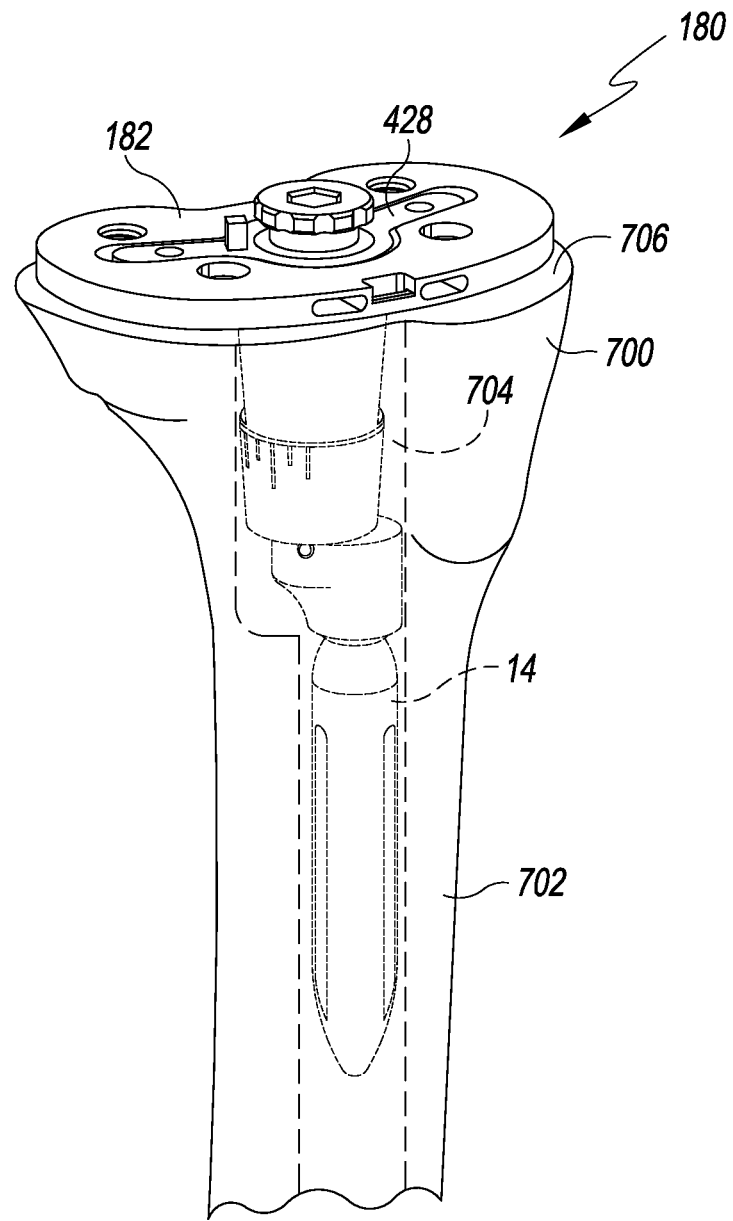
Figure 27:
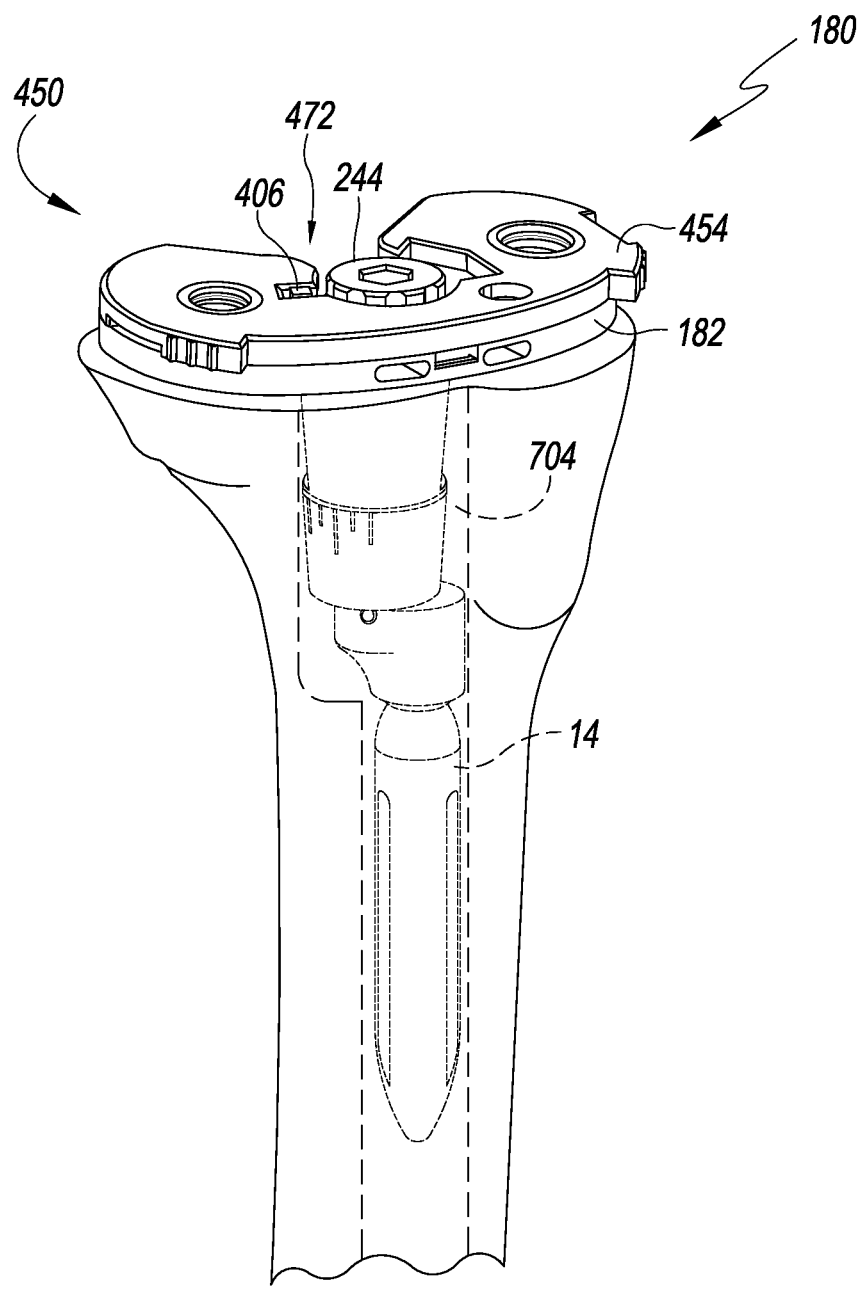

The assembled tibial tray trial 180 may then be inserted into the medullary canal 704 of the patient's tibia 702. To do so, the surgeon may align the stem trial 14 with the proximal opening 710 of the canal 704, which was been enlarged by the reaming operation. The surgeon may then advance the tibial tray trial 180 downward to position the stem trial 14 and the stem adaptor 184 in the medullary canal 704. As shown in FIG. 26, the stem trial 14 and the stem adaptor 184 may be seated in the medullary canal 704 and the tibial base trial 182 engaged with the surgically-prepared proximal surface 706 of the tibia 702.

After the tibial tray trial 180 is positioned, the surgeon may perform a trial reduction. To do so, the surgeon may position a check base insert 428 in the plate opening 198 defined in the tibial base trial 182 as shown in FIG. 26. Once the selected base insert 428 is properly seated, the surgeon may select a trial shim 454 and a tibial bearing surface trial 452.

The surgeon may select a fixed bearing surface trial 452 having the desired configuration (e.g., cruciate retaining, posterior stabilized, etc.) and secure the trial 452 to the shim 454 before or after positioning the shim 454 on the tray trial 180. To position the selected trial shim 454, the surgeon may align the aperture 466 of the shim 454 with the button head 244 of the fastener 242 and the lug 406 of the insert 428. The surgeon may then place the shim 454 over the button head 244 and the lug 406 to seat the shim 454 on the tray trial 180. When properly seated in the fixed bearing orientation, the lug 406 is received in the slot 472 of the shim 454 such that the shim 454 (and hence bearing surface trial 452 when attached) is not permitted to rotate relative to the tray trial 180.

When the fixed bearing surface trial 450 is in place, the surgeon may extend the knee of the patient, noting the anteroposterior stability, medial-lateral stability, and overall alignment in the anterior-posterior ("A/P") plane and medial-lateral ("M/L") plane. Rotational alignment of the tibial base trial 182 may be adjusted by loosing the fastener 242 and moving the knee through the range of motion. The surgeon sets the rotation of the base trial 182 by assessing multiple factors including femoral position and tibial plateau coverage [team: does this occur with in an offset procedure?]. The surgeon may continue to try various combinations of shims 454 and bearing surface trials 452 to ascertain which implant size and configuration (e.g., the thickness of the implant, the mobility of the implant, etc.) will have the best stability in flexion and extension while permitting the desired kinematics. After completing the trial reduction, the surgeon may fix the tibial tray trial 182 into position by inserting one or more fixation pins into the fastener guides 234.

Figure 28:
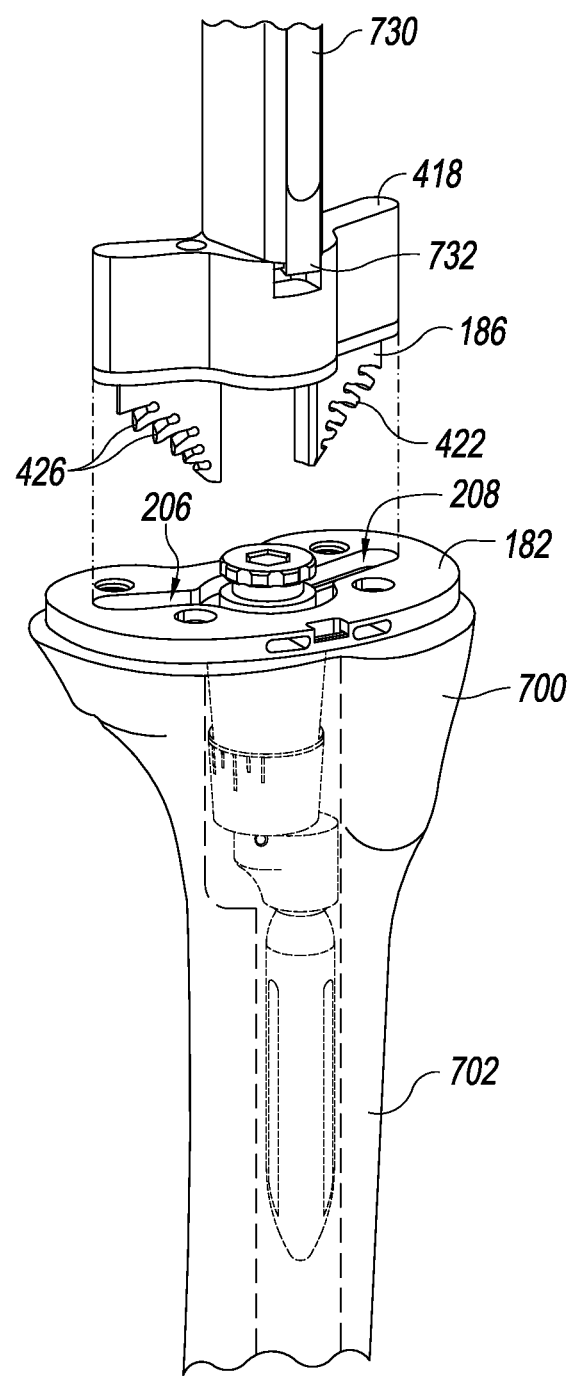

The surgeon may continue tibial preparation by impacting the keel punch insert 186 into the proximal end 700 of the tibia 702. To do so, the surgeon removes the check insert 428 from the base trial 182, as shown in FIG. 28. The surgeon may then secure the punch insert 186 to the attachment tool 418 by aligning the pegs 416 with the bores 414 of the base insert 186 and advancing the pegs 416 into the bores 414.

The surgeon may secure the attachment tool 418 to an impaction handle 730 by engaging a catch 732 and a rod (not shown) of the impaction handle 730 with the socket 444 formed on the attachment tool 418. After securing the handle 730 to the tool 418 (and hence the punch insert 186), the surgeon may align the prongs 410, 412 of the punch insert 186 with the passageways 206, 208 defined in the base trial 182. The surgeon may then advance the punch insert 186 downward such that the lower arms 422 pass through the passageways 206, 208 and the teeth 426 engage the proximal end 700 of the tibia 702.

The surgeon may then drive the punch insert 186 into the tibia 702 by striking the handle 730 with mallet, sledge, or other impaction tool. As the punch insert 186 is driven into the bone, the cutting teeth 426 of the punch insert 186 engage the patient's tibia 702 to form additional slots (not shown) in the tibia 702. When the punch insert 186 is seated on the tibial base trial 182, the lower arms 422 extend outwardly from the slot 278 defined in the stem adaptor 184.

After the keel punch insert 186 has been driven into the tibia 702, the surgeon may remove the tibial tray trial 180 and the punch insert 186 from the proximal end 700 of the patient's tibia 702. To do so, the surgeon may attach the removal tool 500 to the tibial tray trial 180 by aligning the knob 256 of the fastener 242 with the slot 530 of the removal tool 500. The removal tool 500 may then be advanced over the knob 256 such that the neck 254 is received between the engagement arms 532 and the knob 256 is positioned in the slot 530. As the removal tool 500 is moved into engagement with the tray trial 180, the knob 256 engages a cam surface 740 (see FIG. 17) of the dowel pin 544, thereby causing the lever 542 to pivot about the axis 554 such that the dowel pin 544 is advanced into the socket 258 of the fastener 242. When the dowel pin 544 is received in the socket 257, the biasing element 566 urges the lever 542 into the locked position to secure the tray trial 180 to the removal tool 500.

Figure 29:
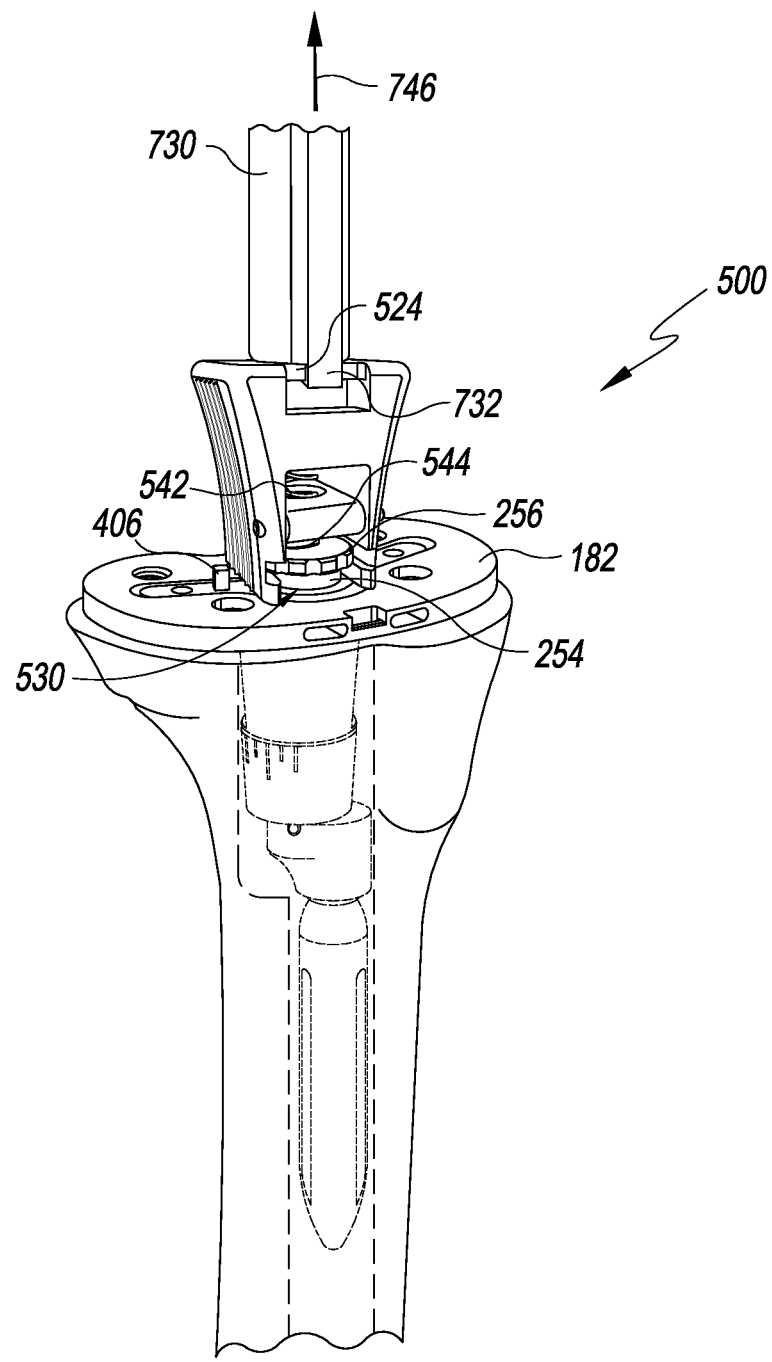

The removal tool 500 may also be secured to the impaction handle 730, as shown in FIG. 29. To do so, the surgeon may engaging the catch 732 of the handle 730 with flange 524 of the removal tool 500 and the rod of the handle 730 with the central aperture 512 formed on the attachment tool 418. When the removal tool 500 is positioned as shown in FIG. 29, the surgeon may pull in the direction indicated by arrow 746 to disengage the tibial tray trial 180 and the punch insert 186 from the tibia 702. It should be appreciated that the removal tool 500 may be attached in another orientation relative to the tibial tray trial 180 such that, for example, the slot 530 faces posteriorly rather than anteriorly as shown in FIG. 29.

The surgeon may then detach the tibial tray trial 180 and the punch insert 186 from the removal tool 500 by operating the actuation arm 548 of the lever 542 as described above. The surgeon may then proceed with the implantation of the prosthesis 600.

Figure 31:
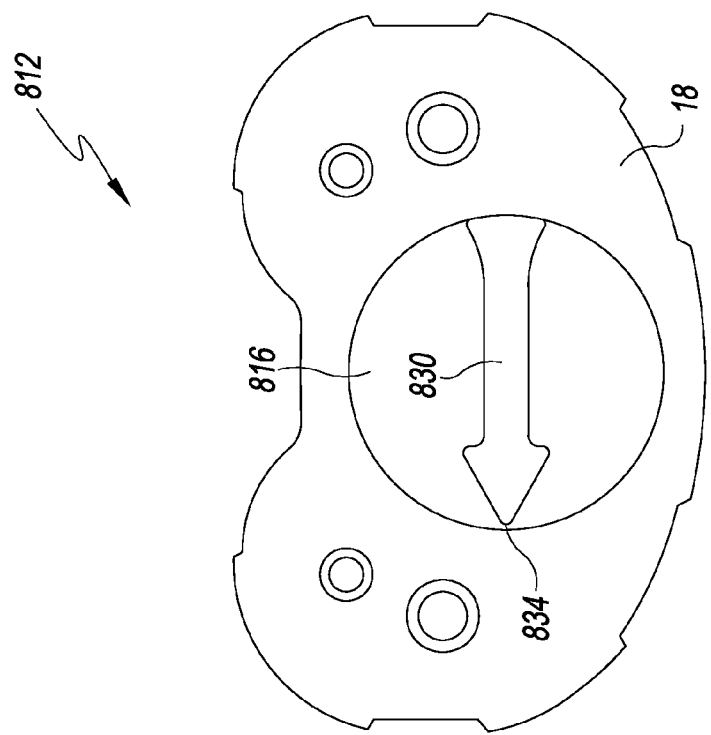
FIG. 31 is a top plan view of the embodiment of FIG. 30.
Figure 30:
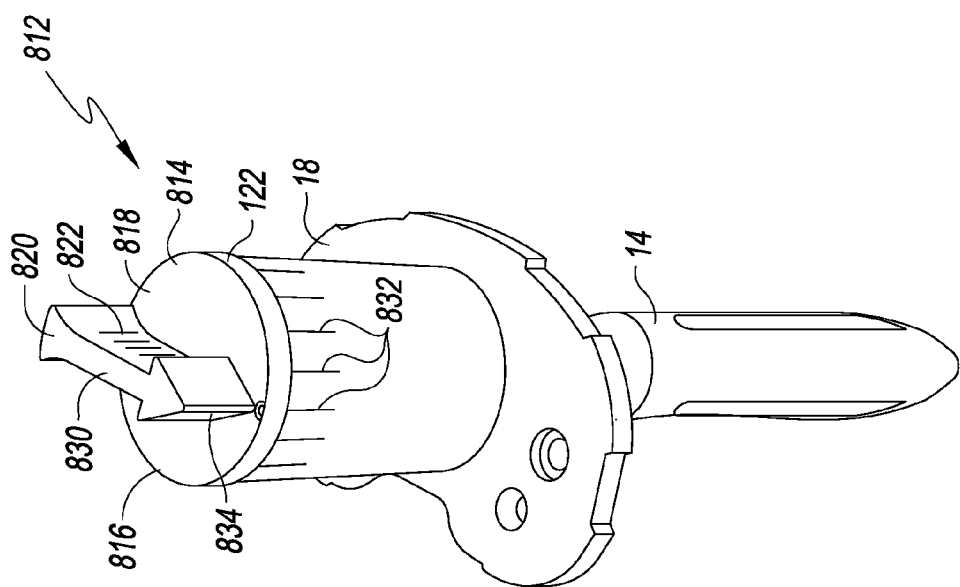
FIG. 30 is a perspective view of another embodiment of the offset guide instrument assembly.

Referring now to FIGS. 30-31, another embodiment of an offset guide instrument assembly (hereinafter instrument assembly 812) is shown. The embodiment of FIGS. 30-31 is similar to the embodiment of FIGS. 1-29. As such, the same reference numbers will be used in FIGS. 30-31 to refer to the same features in the FIGS. 1-29. As shown in FIG. 30, the instrument assembly 812 includes a guide tower 18, a stem trial 14, and an offset guide tool 814 removably coupled to the stem trial 14. Like the offset guide tool 76, the offset guide tool 814 has a barrel body 80 sized to be received in the passageway 54 of the guide tower 18 and a shaft 82 attached to the barrel body 80. The shaft 82 is configured to be coupled to the stem trial 14.

The offset guide tool 814 also includes a knob 816 attached to the upper end 86 of the barrel body 80. As shown in FIG. 30, the knob 816 includes an annular flange 122, which is sized to engage the guide tower 18. The knob 816 also includes an upper surface 818 positioned opposite the annular flange 122 and a boss 820 that extends upwardly from the upper surface 818. The boss 820 includes a contoured outer surface 822, which may be gripped by the surgeon or other user to rotate the offset guide tool 814 when the barrel body 80 is received in the guide tower 18.

The offset guide instrument assembly 812 includes an offset indicator 830 configured to indicate the offset orientation between the stem trial 14 and the guide tower 18. As shown in FIG. 30, the offset indicator 830 includes the boss 820 of the knob 816 and a plurality of markings 832 defined on the guide tower 18. The boss 820 is arrow-shaped and includes a tip 834 that may be aligned with any of the markings 832. Like the markings 142 of FIGS. 1-29, each marking 832 on the guide tower 18 corresponds to a different offset orientation.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of surgically preparing a patient's tibia, the method comprising:
   positioning a guide tower on a surgically-prepared proximal surface above an opening of a medullary canal of the patient's tibia,
   attaching a stem trial to a lower end of an offset tool that is sized to be received in the guide tower,
   advancing the stem trial through the guide tower and the surgically-prepared proximal surface into the medullary canal,
   rotating the offset tool to move the guide tower to a desired offset orientation on the surgically-prepared proximal surface,
   securing the guide tower to the patient's tibia at the desired offset orientation,
   removing the offset tool and the stem trial from the patient's tibia,
   advancing a reamer through the guide tower into the medullary canal,
   positioning a tibial base trial on the surgically-prepared proximal surface based on the desired offset orientation, and
   attaching the stem trial to a stem adaptor, and securing the stem adaptor to the tibial base trial, wherein positioning the tibial base trial on the surgically-prepared proximal surface includes inserting the stem adaptor and the stem trial into the medullary canal.

2. The method of claim 1, further comprising:
   identifying a first offset indicator on the guide tower and the offset tool when the guide tower is in the desired offset orientation, and
   identifying a second offset indicator on the stem adaptor corresponding to the first offset indicator,
   rotating a first adaptor body of the stem adaptor relative to a second adaptor body to a position associated with the second offset indicator, and
   securing the first adaptor body in the position relative to the second adaptor body before inserting the stem adaptor and the stem trial into the medullary canal.

3. The method of claim 2, wherein the first adaptor body defines a first axis, the second adaptor body defines a second axis, and moving the tibial base trial on the surgically-prepared proximal surface includes moving the first axis in a circular path about the second axis.

4. The method of claim 3, wherein securing the stem adaptor to the tibial base trial and securing the first adaptor body in the position relative to the second adaptor body includes advancing a threaded shaft pivotally coupled to the tibial base trial into a threaded aperture of the stem adaptor.

5. The method of claim 1, wherein rotating the offset tool to move the guide tower to the desired offset orientation includes moving the guide tower in a circular path.

6. The method of claim 1, wherein:
   the guide tower defines a first axis,
   the stem trial defines a second axis, and
   rotating the offset tool to move the guide tower on the surgically-prepared proximal surface of the patient's tibia includes moving the first axis in a circular path about the second axis.

7. The method of claim 1, further comprising inserting a keel punch through a slot defined in the tibial base trial into the surgically-prepared proximal surface of the patient's tibia.

8. The method of claim 7, further comprising positioning a tibial bearing trial over a lug of formed on the keel punch on the tibial base trial.

9. A method of surgically preparing a patient's tibia, the method comprising:
   positioning a guide tower on a surgically-prepared proximal surface above an opening of a medullary canal of the patient's tibia, the guide tower defining a first axis,
   attaching a stem trial to a lower end of an offset tool that is sized to be received in the guide tower,
   advancing the stem trial through the guide tower and the surgically-prepared proximal surface into the medullary canal, the stem trial defining a second axis parallel to the first axis,
   rotating the offset tool in the guide tower to move the guide tower on the surgically-prepared proximal surface such that the first axis is moved in a circular path about the second axis,
   identifying a desired offset orientation of the guide tower,
   adjusting a stem adaptor based on the desired offset orientation,
   securing the stem trial to the stem adaptor,
   inserting the stem adaptor and the stem trial into the medullary canal, and
   engaging the surgically-prepared proximal surface with a tibial base trial secured to the stem adaptor.

10. The method of claim 9, wherein adjusting the stem adaptor includes rotating a first adaptor body relative to a second adaptor body.

11. The method of claim 10, wherein:
    identifying the desired offset orientation of the guide tower includes identifying a first offset indicator corresponding to the desired offset orientation,
    adjusting the stem adaptor includes identifying a second offset indicator on the stem adaptor corresponding to the desired offset orientation, and
    rotating the first adaptor body relative to the second adaptor body includes moving the first adaptor body to a rotational position associated with the second offset indicator.

12. The method of claim 10, further comprising evaluating tibial base trial on the surgically-prepared proximal surface of the patient's tibia, and rotating the first adaptor body relative to the second adaptor body to move the tibial base trial on the surgically-prepared proximal surface of the patient's tibia.

13. The method of claim 9, further comprising inserting a keel punch through a slot defined in the tibial base trial into the surgically-prepared proximal surface of the patient's tibia.

14. The method of claim 13, wherein inserting the keel punch through the slot defined in the tibial base trial and into the surgically-prepared proximal surface of the patient's tibia includes inserting a portion of the keel punch into a slot defined in the stem adaptor.

15. A method of performing an orthopaedic surgical procedure on a patient's tibia, the method comprising:
   securing a stem trial to a stem adaptor,
   advancing a fastener secured to a tibial base trial into a threaded aperture of the stem adaptor such that the stem adaptor is secured to the tibial base trial,
   rotating a first adaptor body of the stem adaptor relative to a second adaptor body of the stem adaptor to position the stem adaptor in a desired offset orientation,
   advancing the fastener deeper into the threaded aperture to lock the first adaptor body and the second adaptor body in the desired offset orientation,
   inserting the stem adaptor and the stem trial through a surgically-prepared proximal surface of the patient's tibia into a medullary canal of the patient's tibia, and
   engaging the tibial base trial with the surgically-prepared proximal surface.

16. The method of claim 15, further comprising:
   positioning a base plate on the surgically-prepared proximal surface, the base plate including a plurality of surface sections shaped to match surfaces of a prosthetic tibial tray,
   advancing an offset tool through an opening in the base plate, and
   rotating the offset tool to move the base plate on the surgically-prepared proximal surface to determine the desired offset orientation.

17. The method of claim 16, wherein:
   rotating the offset tool to move the base plate comprises identifying a first offset indicator corresponding to the desired offset orientation, and
   rotating the first adaptor body of the stem adaptor relative to the second adaptor body includes identifying a second offset indicator on the stem adaptor corresponding to the desired offset orientation.

18. The method of claim 15, further comprising inserting a keel punch through a slot defined in the tibial base trial into the surgically-prepared proximal surface of the patient's tibia.

19. The method of claim 18, further comprising positioning a tibial bearing trial over a lug of formed on the keel punch on the tibial base trial.

* * * * *